United States Patent
Miller et al.

(10) Patent No.: US 12,109,236 B2
(45) Date of Patent: Oct. 8, 2024

(54) MANIPULATING ARID5B EXPRESSION IN IMMUNE CELLS TO PROMOTE METABOLISM, SURVIVAL, AND FUNCTION

(71) Applicant: REGENTS OF THE UNIVERSITY OF MINNESOTA, Minneapolis, MN (US)

(72) Inventors: Jeffrey Steven Miller, Minneapolis, MN (US); Frank Martin Cichocki, Minneapolis, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 852 days.

(21) Appl. No.: 17/055,525

(22) PCT Filed: May 8, 2019

(86) PCT No.: PCT/US2019/031296
§ 371 (c)(1),
(2) Date: Nov. 13, 2020

(87) PCT Pub. No.: WO2019/221991
PCT Pub. Date: Nov. 21, 2019

(65) Prior Publication Data
US 2021/0154232 A1 May 27, 2021

Related U.S. Application Data

(60) Provisional application No. 62/670,962, filed on May 14, 2018.

(51) Int. Cl.
| | | |
|---|---|---|
| A61K 35/17 | (2015.01) | |
| C07K 14/47 | (2006.01) | |
| C07K 14/725 | (2006.01) | |
| C12N 5/00 | (2006.01) | |
| C12N 5/0783 | (2010.01) | |

(52) U.S. Cl.
CPC .............. *A61K 35/17* (2013.01); *C07K 14/47* (2013.01); *C07K 14/7051* (2013.01); *C12N 5/0646* (2013.01); *C12N 2510/00* (2013.01)

(58) Field of Classification Search
CPC .............................. A61K 35/17; C12N 5/0646
See application file for complete search history.

(56) References Cited

U.S. PATENT DOCUMENTS

| 5,837,492 A | 11/1998 | Tavtigian |
| 2002/0190663 A1 | 12/2002 | Rasmussen |
| 2011/0206708 A1 | 8/2011 | Har-Noy |

FOREIGN PATENT DOCUMENTS

| WO | 2017048809 | 3/2017 | |
| WO | WO 2017/048809 A1 * | 3/2017 | ............. A61K 35/17 |
| WO | 2017112877 A1 | 6/2017 | |
| WO | 2017192440 | 11/2017 | |

OTHER PUBLICATIONS

Glienke et al. (2015) "Advantages and applications of CAR-expressing natural killer cells" Frontiers in pharmacology, 6, 21. (Year: 2015).*
Leong et al. (2017) "ARID5B as a critical downstream target of the TAL1 complex that activates the oncogenic transcriptional program and promotes T-cell leukemogenesis" Genes & development, 31(23-24), 2343-2360. (Year: 2017).*
Feng et al. (2005) "The recombination activation gene 1 (Rag1) is expressed in a subset of zebrafish olfactory neurons but is not essential for axon targeting or amino acid detection" BMC neuroscience, 6(1), 1-12. (Year: 2005).*
Cichocki et al. (Jul. 30, 2018) "ARID5B regulates metabolic programming in human adaptive NK cells" Journal of Experimental Medicine, 215(9), 2379-2395. (Year: 2018).*
Baba, A., et al. 2011. PKA-dependent regulation of the histone lysine demethylase complex PHF2-ARID5B. Nat. Cell. Biol. 13:668-675.
Bergerson RJ, et al. 2016. Fewer Circulating Natural Killer Cells 28 Days After Double Cord Blood Transplantation Predicts Inferior Survival and IL-15 Response. Blood Adv. 1:208-218.
Buck, M.D., et al. 2016. Mitochondrial Dynamics Controls T Cell Fate through Metabolic Programming. Cell. 166:63-76.
Champagne, D.P., et al. 2016. Fine-Tuning of CD8(+) T Cell Mitochondrial Metabolism by the Respiratory Chain Repressor MCJ Dictates Protection to Influenza Virus. Immunity. 44:1299-1311.
Chen, G., et al. "Chemically defined conditions for human iPSC derivation and culture." Nature methods 8.5 (2011):424-429.
Cichocki F, et al. 2016. CD56dimCD57+NKG2C+ NK cell expansion is associated with reduced leukemia relapse after reduced intensity HCT. Leukemia. 30:456-462.
Claussnitzer, M., et al. 2015. FTO Obesity Variant Circuitry and Adipocyte Browning in Humans. N. Engl. J. Med. 373:895-907.
Corat MA, et al. 2017. Acquired somatic mutations in PNH reveal long-term maintenance of adaptive NK cells independent of HSPCs. Blood. 129:1940-1946.
Cunningham, J.T., et al. 2007. mTOR controls mitochondrial oxidative function through a YY1-PGC-1alpha transcriptional complex. Nature. 450:736-740.

(Continued)

*Primary Examiner* — Teresa E Knight
*Assistant Examiner* — James Joseph Graber
(74) *Attorney, Agent, or Firm* — Fish & Richardson P.C.

(57) ABSTRACT

Provided herein are methods of manipulating ARID5B expression in immune cells such NK cells, T cells, and T cell and NK cell progenitors to enhance their persistence and function in vivo. Also provided herein are modified immune cells and compositions comprising such modified cells for anti-cancer, anti-viral, and other immunotherapies. In some embodiments, immune cells are genetically modified to increase ARID5B expression and, thus, improve persistence, increase in vivo anti-tumor efficacy, and increase viability and functionality of the modified cells after freezing and thawing.

12 Claims, 21 Drawing Sheets
Specification includes a Sequence Listing.

(56) References Cited

OTHER PUBLICATIONS

Ebert, A. D., et al. "Induced pluripotent stem cells from a spinal muscular atrophy patient." Nature 457.7227 (2009):277-280.
Falkenberg, M., et al. 2002. Mitochondrial transcription factors B1 and B2 activate transcription of human mtDNA. Nat. Genet. 31:289-294.
Foley B, et al. 2012. Cytomegalovirus reactivation after allogeneic transplantation promotes a lasting increase in educated NKG2C+ natural killer cells with potent function. Blood. 119:2665-2674.
Gerencser, A.A., et al. 2009. Quantitative microplate-based respirometry with correction for oxygen diffusion. Anal. Chem. 81:6868-6878.
Gimenez-Cassina, A., et al. 2015. Regulation of mitochondrial nutrient and energy metabolism by BCL-2 family proteins. Trends. Endocrinol. Metab. 26:165-175.
Guma, M., et al. 2004. Imprint of human cytomegalovirus infection on the NK cell receptor repertoire. Blood. 104:3664-3671.
Haut, S., et al. 2003. A deletion in the human QP-C gene causes a complex III deficiency resulting in hypoglycaemia and lactic acidosis. Hum. Genet. 113:118-122.
Howden, S. E., et al. "Genetic correction and analysis of induced pluripotent stem cells from a patient with gyrate atrophy." Proceedings of the National Academy of Sciences 108.16 (2011): 6537-6542.
Huss, J.M., et al. 2004. Estrogen-related receptor alpha directs peroxisome proliferator-activated receptor alpha signaling in the transcriptional control of energy metabolism in cardiac and skeletal muscle. Mol. Cell. Biol. 24:9079-9091.
International Searching Authority. International Search Report and Written Opinion for application PCT/US2019/031296. Mailed on Aug. 5, 2019. 10 pages.
Jones, A., et al. "Cryopreservation of metaphase II human oocytes effects mitochondrial membrane potential: Implications for developmental competence." Human Reproduction 19.8 (2004): 1861-1866.
Kagi, D., et al. 1994. Cytotoxicity mediated by T cells and natural killer cells is greatly impaired in perforin-deficient mice. Nature. 369:31-37.
Knorr, D. A., et al. "Clinical-scale derivation of natural killer cells from human pluripotent stem cells for cancer therapy." Stem cells translational medicine 2.4 (2013): 274-283.
Kortschak, R.D., et al. 2000. ARID proteins come in from the desert. Trends. Biochem. Sci. 25:294-299.
Lahoud, M.H., et al. 2001. Gene targeting of Desrt, a novel ARID class DNA-binding protein, causes growth retardation and abnormal development of reproductive organs. Genome. Res. 11:1327-1334.
Larsson, N.G., et al. 1998. Mitochondrial transcription factor A is necessary for mtDNA maintenance and embryogenesis in mice. Nat. Genet. 18:231-236.
Lee, J. et al. 2015. Epigenetic modification and antibody-dependent expansion of memory-like NK cells in human cytomegalovirus-infected individuals. Immunity. 42:431-442.
Leong, W.Z., et al. 2017. ARID5B as a critical downstream target of the TAL 1 complex that activates the oncogenic transcriptional program and promotes T-cell leukemogenesis. Genes. Dev. 31:2343-2360.
Li, F., et al. 2005. Myc stimulates nuclearly encoded mitochondrial genes and mitochondrial biogenesis. Mol. Cell. Biol. 25:6225-6234.
Liu, Y., et al. 2017. Blood monocyte transcriptome and epigenome analyses reveal loci associated with human atherosclerosis. Nat. Comm. 8:393.
Lopez-Verges, S., et al. 2011. Expansion of a unique CD57(+)NKG2Chi natural killer cell subset during acute human cytomegalovirus infection. Proc. Natl. Acad. Sci. U. S. A. 108:14725-14732.
Lu, B., et al. "Long-term safety and function of RPE from human embryonic stem cells in preclinical models of macular degeneration." Stem cells 27.9 (2009): 2126-2135.
Sun, J.C., et al. 2009. Adaptive immune features of natural killer cells. Nature. 457:557-561.

Marcais, A., et al. 2014. The metabolic checkpoint kinase mTOR is essential for IL-15 signaling during the development and activation of NK cells. Nat. Immunol. 15:749-757.
Mekler, P., et al. "The use of recombinant DNA technology to study gene alteration." Mutation Research/Reviews in Genetic Toxicology 153.1-2 (1985): 13-55.
Miller JS, et al. 2005. Successful adoptive transfer and in vivo expansion of human haploidentical NK cells in patients with cancer. Blood. 105:3051-3057.
Mookerjee, S.A., et al. 2010. Mitochondrial uncoupling and lifespan. Mech. Agein.g Dev. 131:463-472.
Nabekura, T., et al. 2016. Tracking the fate of antigen-specific versus cytokine-activated natural killer cells after cytomegalovirus infection. J. Exp. Med. 213:2745-2758.
Ng, E. S., et al. "A protocol describing the use of a recombinant protein-based, animal product-free medium (APEL) for human embryonic stem cell differentiation as spin embryoid bodies." Nature protocols 3.5 (2008): 768-776.
Nicholls, D.G. 2009. Spare respiratory capacity, oxidative stress and excitotoxicity. Biochem. Soc. Trans. 37:1385-1388.
Pena, F. J., et al. "Antioxidant supplementation in vitro improves boar sperm motility and mitochondrial membrane potential after cryopreservation of different fractions of the ejaculate." Animal reproduction science 78.1-2 (2003):85-98.
Perry, S.W., et al. 2011. Mitochondrial membrane potential probes and the proton gradient: a practical usage guide. Biotechniques. 50:98-115.
Puigserver, P., et al. 1998. A cold-inducible coactivator of nuclear receptors linked to adaptive thermogenesis. Cell. 92:829-839.
Redondo-Pachon, D., et al. 2017. Adaptive NKG2C+ NK Cell Response and the Risk of Cytomegalovirus Infection In Kidney Transplant Recipients. J. Immunol. 198:94-101.
Saeed, S., et al. 2014. Epigenetic programming of monocyte-to-macrophage differentiation and trained innate Immunity. Science. 345:1251086.
Schlums H, et al. 2015. Cytomegalovirus infection drives adaptive epigenetic diversification of NK cells with altered signaling and effector function. Immunity. 42:443-456.
Schlums H, et al. 2017. Adaptive NK cells can persist in patients with GATA2 mutation depleted of stem and progenitor cells. Blood. 129:1927-1939.
Sentman, C.L., et al. 1991. Bcl-2 inhibits multiple forms of apoptosis but not negative selection in thymocytes. Cell. 67:879-888.
Stroh, C., et al. "The role of caspases in cryoinjury: caspase inhibition strongly improves the recovery of cryopreserved hematopoietic and other cells." The FASEB Journal 16.12 (2002): 1651-1653.
Zhang, T., et al. 2013. Cutting Edge: Antibody-Dependent Memory-like NK Cells Distinguished by FcR? Deficiency. J. Immunol. 190:1402-1406.
Van Der Windt, G.J., et al. 2012. Mitochondrial respiratory capacity is a critical regulator of CD8+ T cell memory development. Immunity. 36:68-78.
Van Der Windt, G.J., et al. 2013. CD8 memory T cells have a bioenergetic advantage that underlies their rapid recall ability. Proc. Natl. Acad. Sci. U. S. A. 110:14336-14341.
Vivier, E., et al. 2011. Innate or adaptive immunity? The example of natural killer cells. Science. 331:44-49.
Whitson, R.H., et al. 1999. The novel Mrf-2 DNA-binding domain recognizes a five-base core sequence through major and minor-groove contacts. Biochem. Biophys. Res. Commun. 258:326-331.
Whitson, R.H., et al. 2003. Neonatal mortality and leanness in mice lacking the ARID transcription factor Mrf-2. Biochem. Biophys. Res. Commun. 312:997-1004.
Yu, J., el al. "Human induced pluripotent stem cells free of vector and transgene sequences." Science 324.5928 (2009): 797-801.
Yu, J., et al. "Induced pluripotent stem cell lines derived from human somatic cells." science 318.5858 (2007):1917-1920.
Cichocki et al., "ARID5B regulates metabolic programming in human adaptive NK cells, " J. Exp. Medicine, 215(9):2379-2395, Jul. 30, 2018.
Extended Search Report in European Appln. No. 19803724.4, dated Feb. 9, 2022, 9 pages.

(56) References Cited

OTHER PUBLICATIONS

GenBank Accession No. NM_001244638.1, "*Homo sapiens* AT-rich interaction domain 5B (ARID5B), transcript variant 2, mRNA," dated May 10, 2017, 5 pages.

GenBank Accession No. NM_032199.2, "*Homo sapiens* AT-rich interaction domain 5B (ARID5B), transcript variant 1, mRNA," dated Apr. 23, 2017, 6 pages.

International Preliminary Report on Patentability in International Appln. No. PCT/US2019/031296, mailed on Nov. 26, 2020, 8 pages.

Qian et al., "[Research advances on correlation of ARID5B gene with childhood acute lymphoblastic leukemia—review]," J. Exp. Hematology, Oct. 2012, 20(5):1280-1283 (with English Abstract).

Bantug et al., "Mitochondria-Endoplasmic Reticulum Contact Sites Function as Immunometabolic Hubs that Orchestrate the Rapid Recal Response of Memory CD8+ T Cells," Immunity, Mar. 2018, 48:542-555.

\* cited by examiner

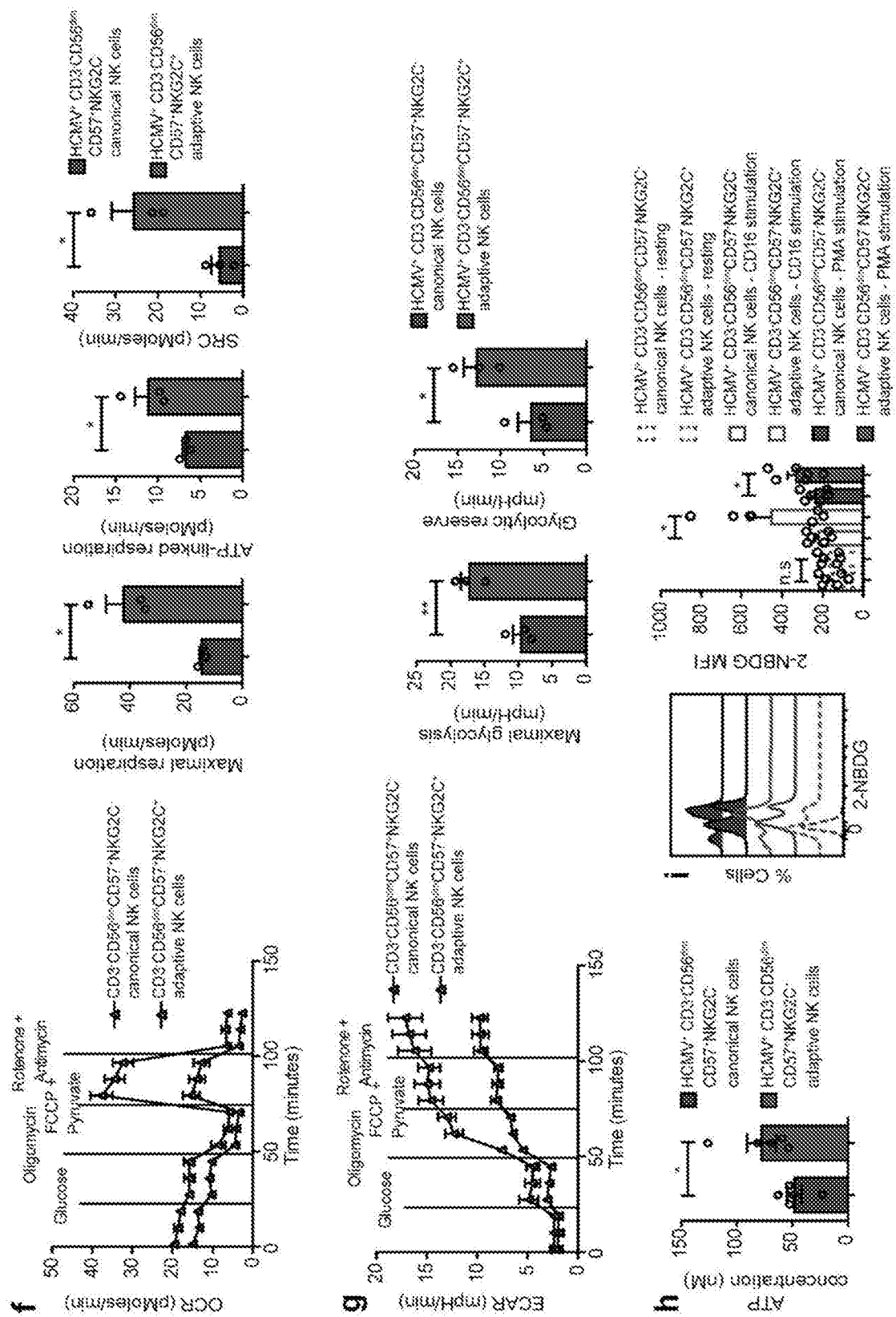
FIGS. 1A-1I, CONTINUED

FIGS. 2A-2G
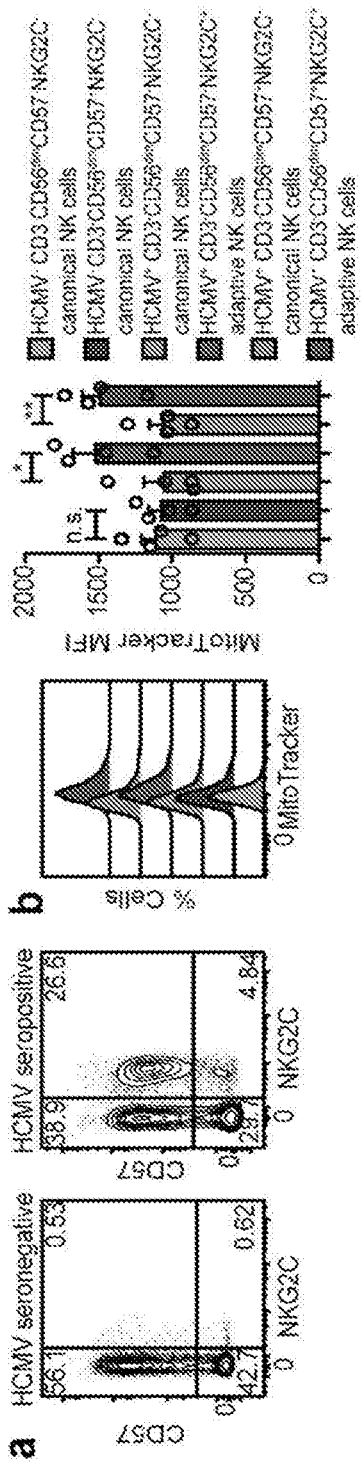
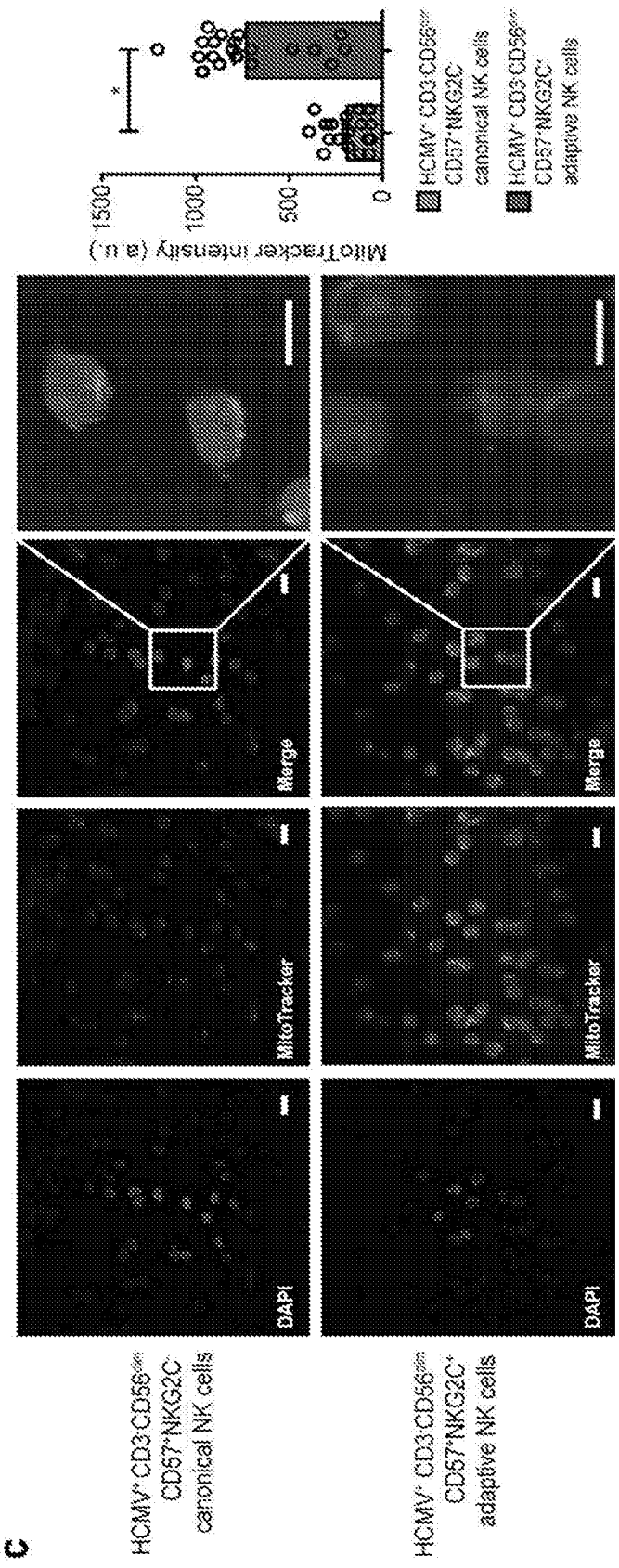

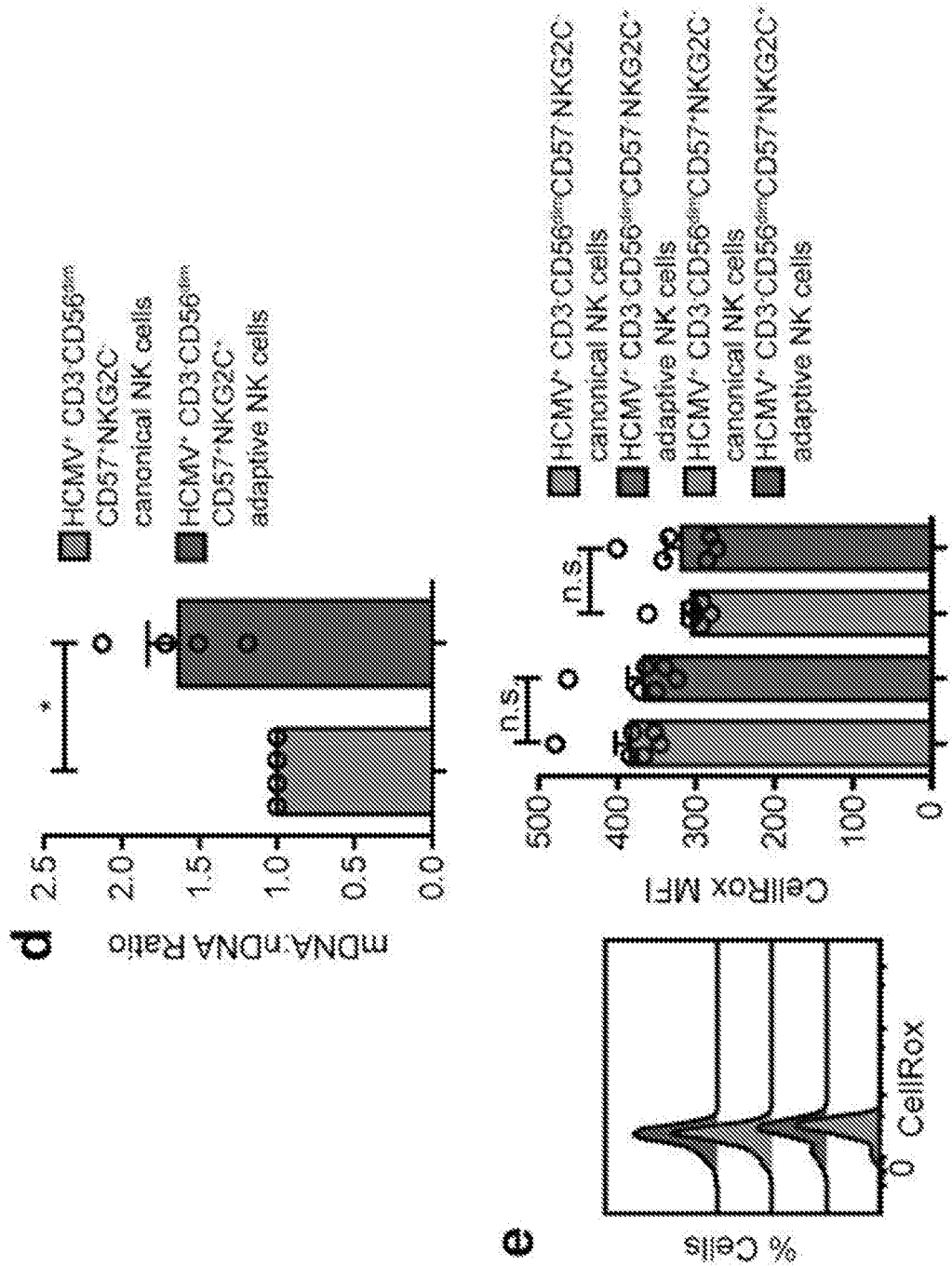
FIGS. 2A-2G, CONTINUED

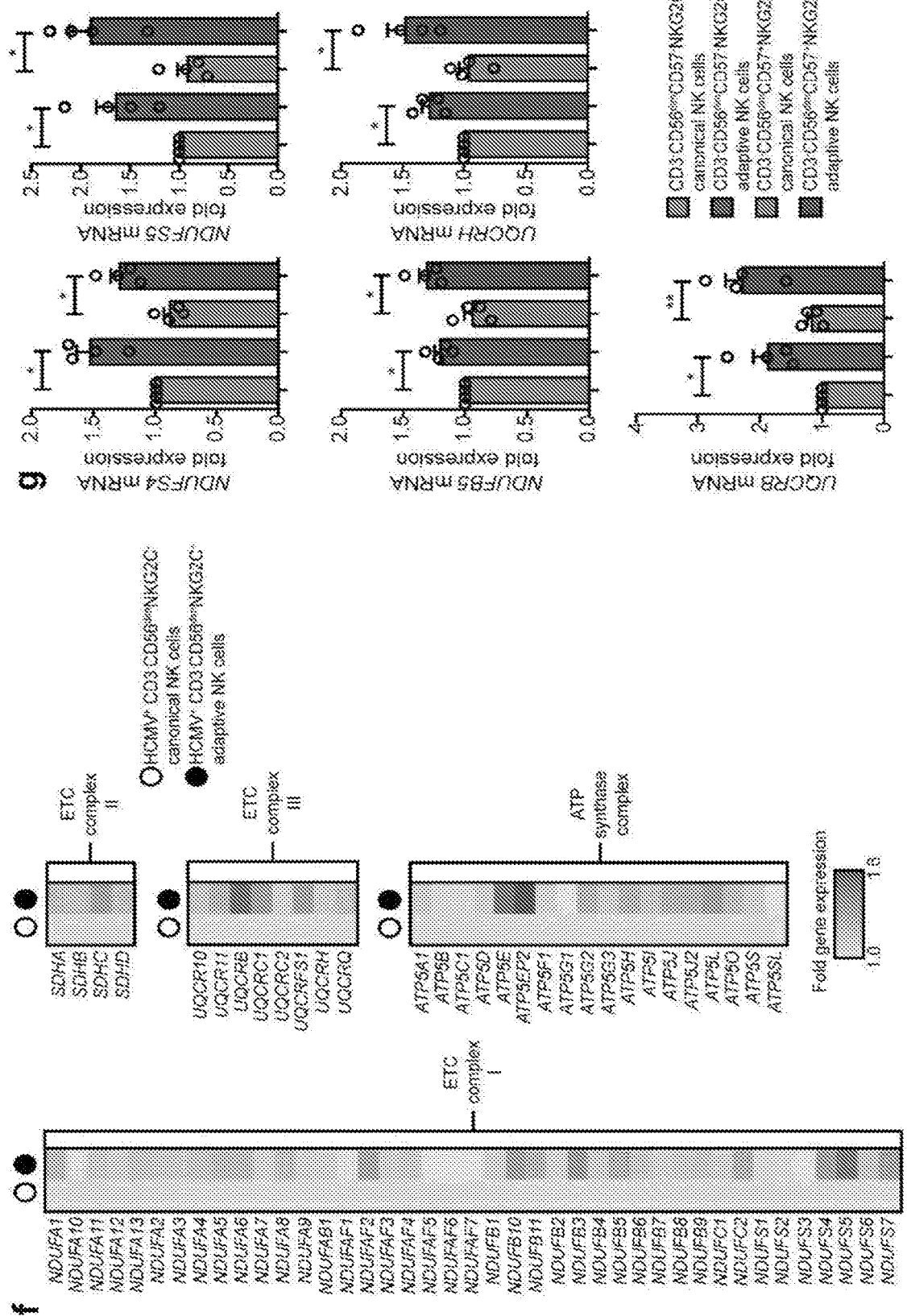
FIGS. 2A-2G, CONTINUED

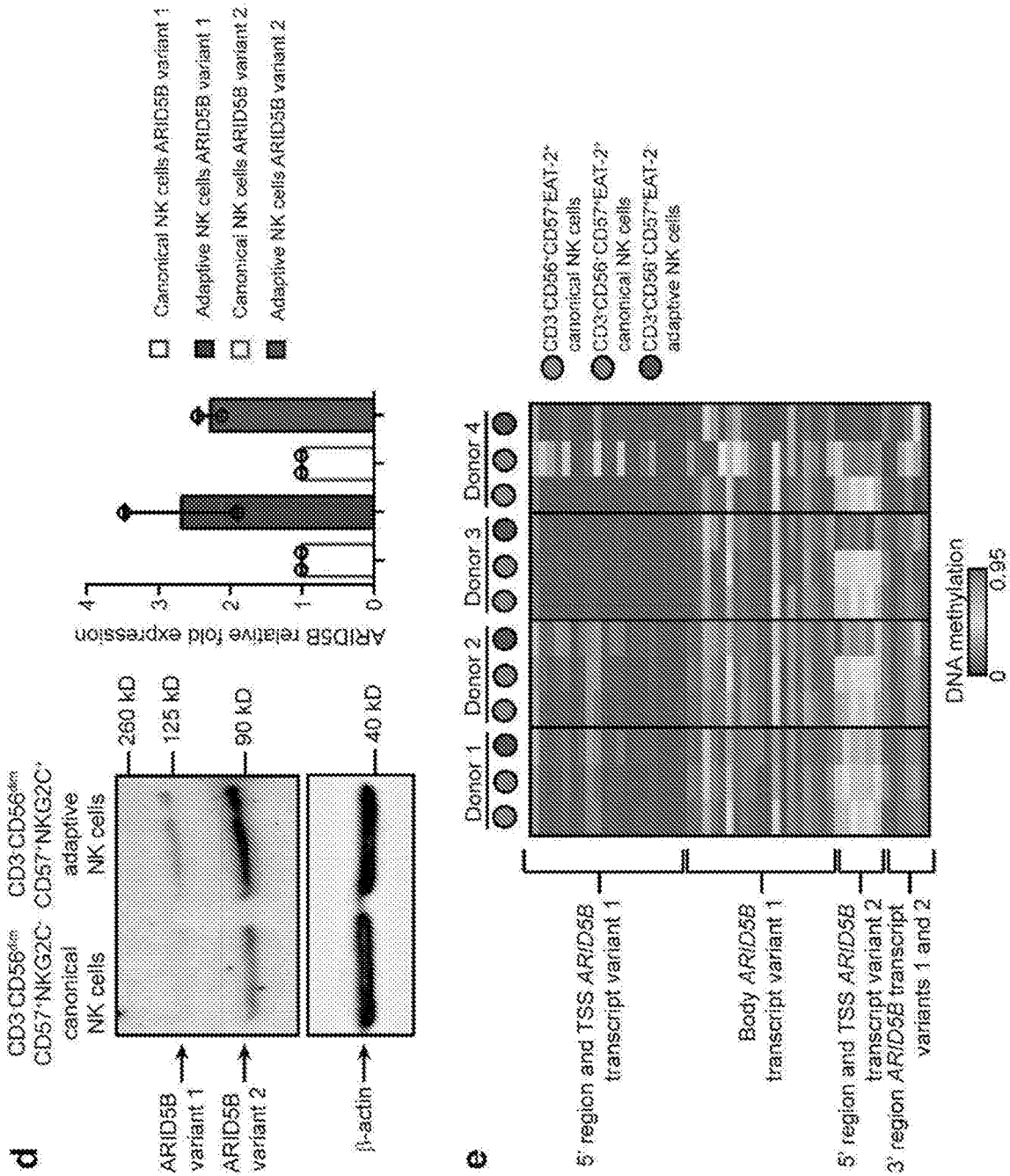
FIGS. 3A-3E, CONTINUED

FIGS. 4A-4H, CONTINUED
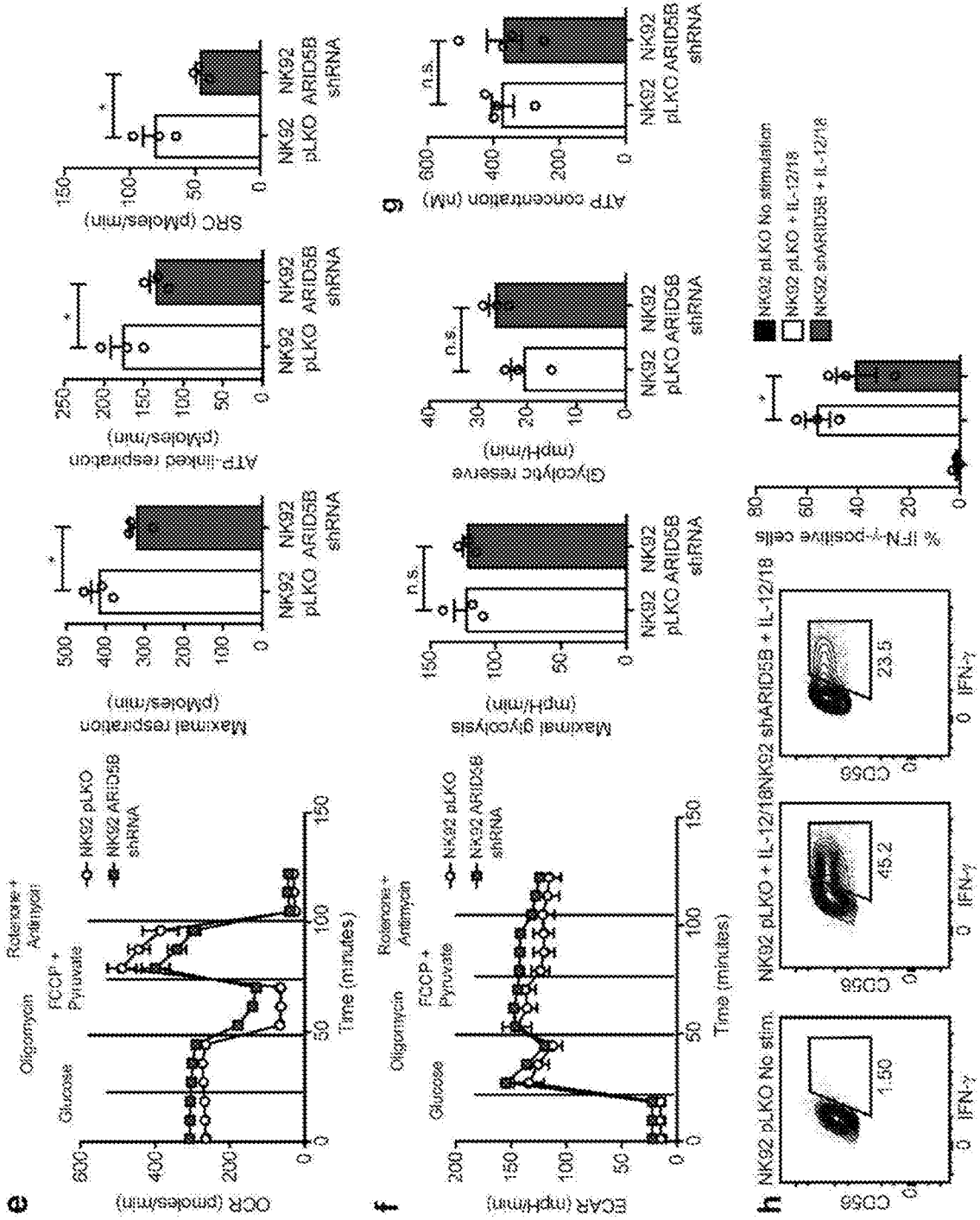

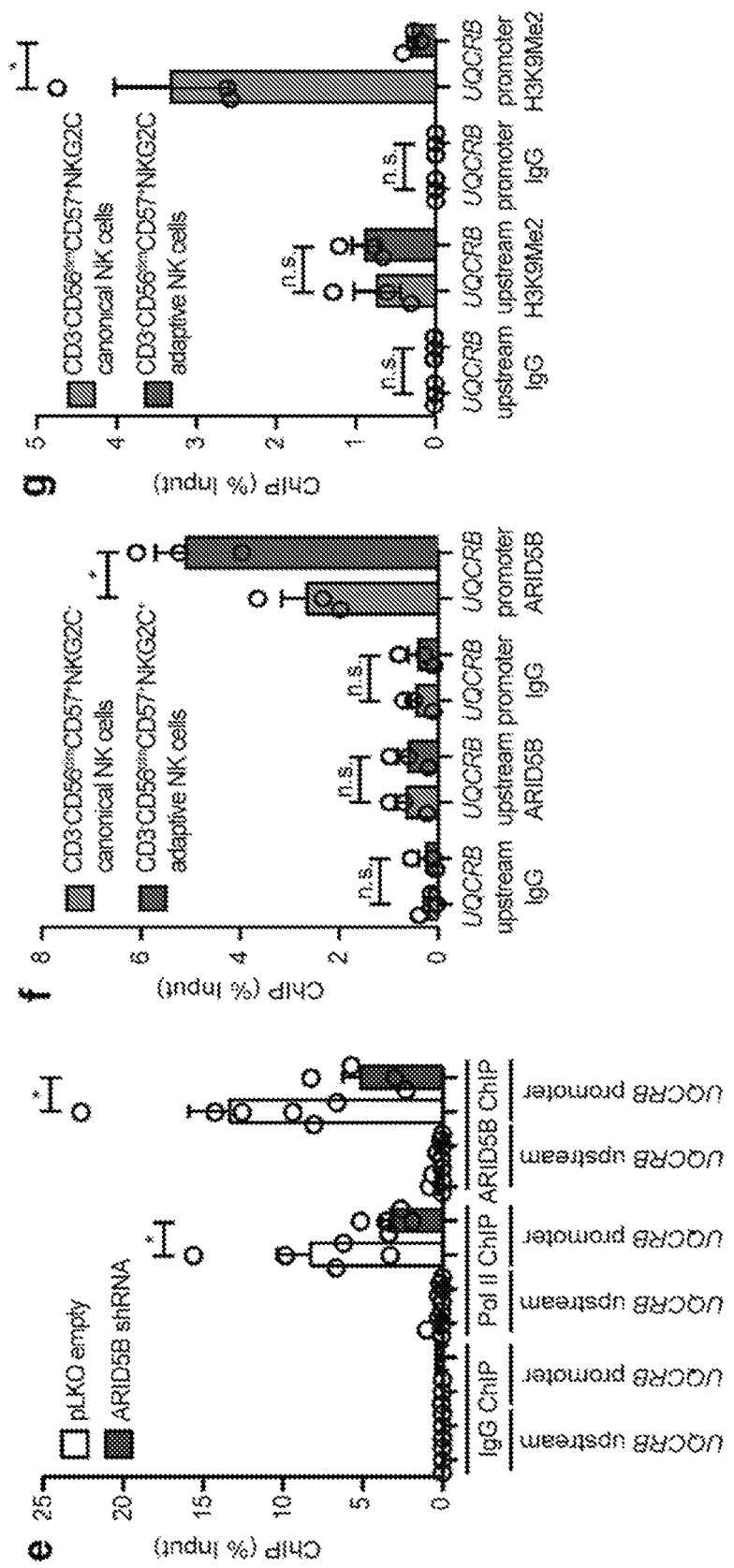
FIGS. 7A-7G, CONTINUED

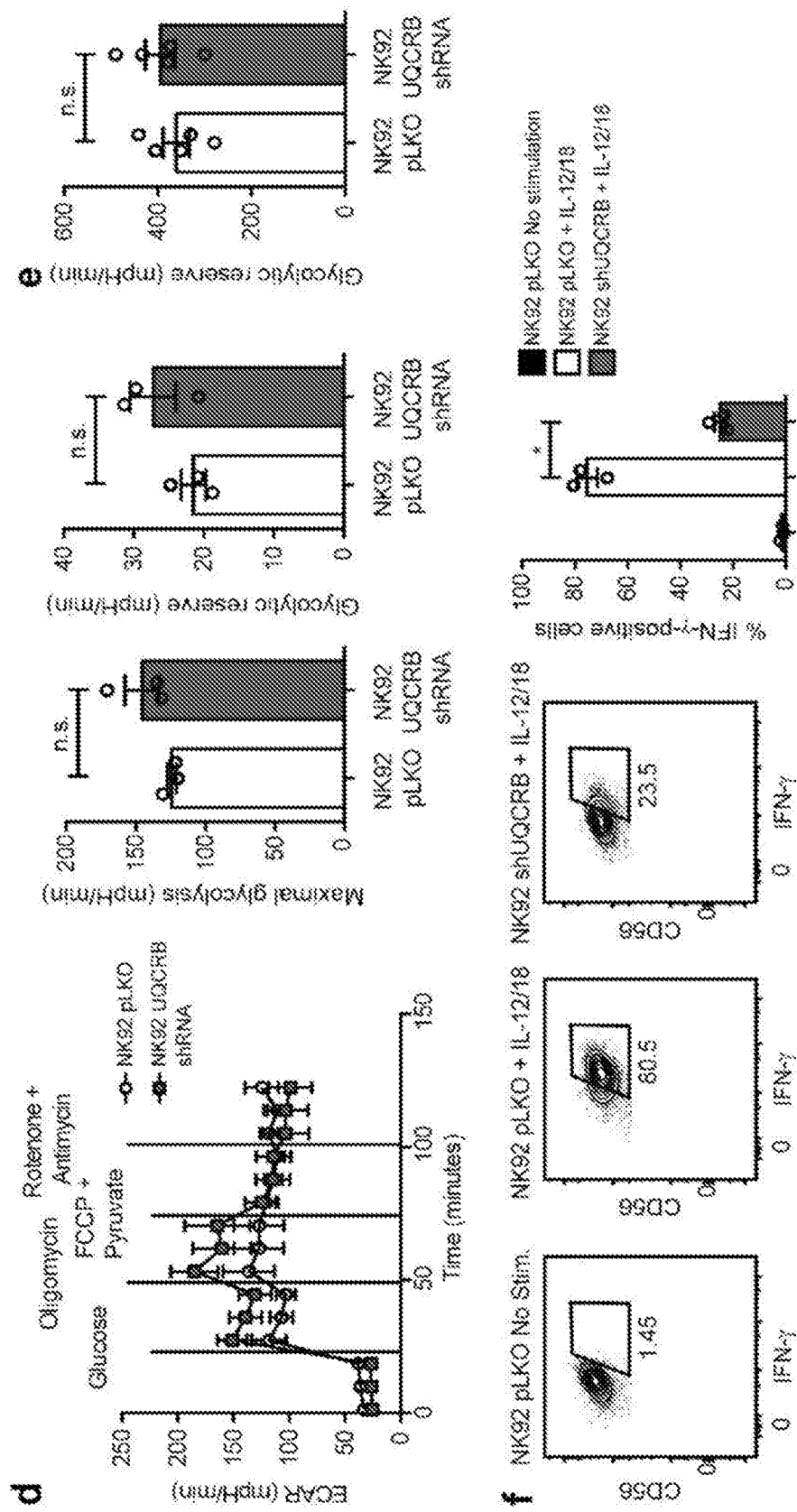
FIGS. 8A-8F, CONTINUED

FIG. 13

| Gene Set | # Genes | Prop. Down | Prop. Up | Direction | p-value (mixed) |
|---|---|---|---|---|---|
| REACTOME_ACYL_CHAIN_REMODELLING_OF_PS | 6 | 0.1666 | 0.5 | Up | 0.0049 |
| REACTOME_SYNTHESIS_OF_VERY_LONG_CHAIN_FATTY_ACYL_COAS | 12 | 0.0833 | 0.3333 | Up | 0.0109 |
| REACTOME_FATTY_ACYL_COA_BIOSYNTHESIS | 15 | 0.0667 | 0.2667 | Up | 0.0361 |
| REACTOME_GLYCOSAMINOGLYCAN_METABOLISM | 69 | .1594 | .0579 | Down | 0.0546 |
| REACTOME_SPHINGOLIPID_DE_NOVO_BIOSYNTHESIS | 27 | 0.1481 | 0.2222 | Up | 0.0052 |
| KEGG_PEROXISOME | 69 | 0.0435 | 0.2029 | Up | 0.0857 |
| KEGG_FATTY_ACID_METABOLISM | 34 | 0.0782 | 0.2059 | Up | 0.1123 |
| KEGG_PANTOTHENATE_AND_COA_BIOSYNTHESIS | 15 | 0.1333 | 0.2 | Up | 0.0131 |
| KEGG_SPHINGOLIPID_METABOLISM | 34 | 0.1471 | 0.2353 | Up | 0.0057 |
| SPHINGOLIPID_METABOLIC_PROCESS | 25 | 0.08 | 0.2 | Up | 0.0474 |
| SPHINGOLIPID_BIOSYNTHETIC_PROCESS | 7 | 0 | 0.2857 | Up | 0.0595 |
| BIOCARTA_MITOCHONDRIAL_PATHWAY | 21 | 0.0476 | 0.1429 | Up | 0.0776 |
| MITOCHONDRIA_MEMBRANE_ORGANIZATION_AND_BIOGENESIS | 11 | 0 | 0.1818 | Up | 0.0889 |
| HALLMARK_FATTY_ACID_METABOLISM | 136 | 0.0756 | 0.1576 | Up | 0.0939 |

SEQUENCE LISTING

```
<160> NUMBER OF SEQ ID NOS: 26

<210> SEQ ID NO 1
<211> LENGTH: 59
<212> TYPE: DNA
<213> ORGANISM: Artificial Sequence
<220> FEATURE:
<223> OTHER INFORMATION: shRNA targeting sequence from ARID5B clone 1040

<400> SEQUENCE: 1
ccgggccttc aaagagaacc atttactcga gtaaatggtt ctctttgaag gcttttttg      59

<210> SEQ ID NO 2
<211> LENGTH: 59
<212> TYPE: DNA
<213> ORGANISM: Artificial Sequence
<220> FEATURE:
<223> OTHER INFORMATION: shRNA targeting sequence from ARID5B clone 1281

<400> SEQUENCE: 2
ccggcgatag aacgaatacc ctattctcga gaatagggta ttcgttctat cgttttttg      59

<210> SEQ ID NO 3
<211> LENGTH: 59
<212> TYPE: DNA
<213> ORGANISM: Artificial Sequence
<220> FEATURE:
<223> OTHER INFORMATION: shRNA targeting sequence from ARID5B clone 2853

<400> SEQUENCE: 3
ccggcgagga agaaacgaac gtgatctcga gatcacgttc gtttcttcct cgttttttg      59

<210> SEQ ID NO 4
<211> LENGTH: 58
<212> TYPE: DNA
<213> ORGANISM: Artificial Sequence
<220> FEATURE:
<223> OTHER INFORMATION: shRNA targeting sequence from UQCRB clone

<400> SEQUENCE: 4
ccggcctaaa gagcagtgga ccaaactcga gtttggtcca ctgctcttta ggttttg        58

<210> SEQ ID NO 5
<211> LENGTH: 20
<212> TYPE: DNA
<213> ORGANISM: Artificial Sequence
<220> FEATURE:
<223> OTHER INFORMATION: ACTB fwd primer

<400> SEQUENCE: 5
cccagcacaa tgaagatcaa                                                 20
```

```
<210> SEQ ID NO 6
<211> LENGTH: 20
<212> TYPE: DNA
<213> ORGANISM: Artificial Sequence
<220> FEATURE:
<223> OTHER INFORMATION: ACTB rev primer

<400> SEQUENCE: 6
acatctgctg gaaggtggac                                               20

<210> SEQ ID NO 7
<211> LENGTH: 23
<212> TYPE: DNA
<213> ORGANISM: Artificial Sequence
<220> FEATURE:
<223> OTHER INFORMATION: NDUFS4 fwd primer

<400> SEQUENCE: 7
ggagctatga cattgaagag agg                                           23

<210> SEQ ID NO 8
<211> LENGTH: 22
<212> TYPE: DNA
<213> ORGANISM: Artificial Sequence
<220> FEATURE:
<223> OTHER INFORMATION: NDUFS4 rev primer

<400> SEQUENCE: 8
tgcacagctg actttattca ca                                            22

<210> SEQ ID NO 9
<211> LENGTH: 20
<212> TYPE: DNA
<213> ORGANISM: Artificial Sequence
<220> FEATURE:
<223> OTHER INFORMATION: NDUFS5 fwd primer

<400> SEQUENCE: 9
gcagcgggat aagctgataa                                               20

<210> SEQ ID NO 10
<211> LENGTH: 21
<212> TYPE: DNA
<213> ORGANISM: Artificial Sequence
<220> FEATURE:
<223> OTHER INFORMATION: NDUFS5 rev primer

<400> SEQUENCE: 10
ctttgacaag gaggtttgtc g                                             21

<210> SEQ ID NO 11
<211> LENGTH: 20
<212> TYPE: DNA
<213> ORGANISM: Artificial Sequence
<220> FEATURE:
<223> OTHER INFORMATION: NDUFB5 fwd primer

<400> SEQUENCE: 11
ctccgaaagc aactcctgac                                               20

<210> SEQ ID NO 12
<211> LENGTH: 20
<212> TYPE: DNA
<213> ORGANISM: Artificial Sequence
<220> FEATURE:
<223> OTHER INFORMATION: NDUFB5 rev primer
```

<400> SEQUENCE: 12
actggaagcc aaactcctca                                              20

<210> SEQ ID NO 13
<211> LENGTH: 25
<212> TYPE: DNA
<213> ORGANISM: Artificial Sequence
<220> FEATURE:
<223> OTHER INFORMATION: UQCRH fwd primer

<400> SEQUENCE: 13
ccacaaactc tttaacaact tgaaa                                         25

<210> SEQ ID NO 14
<211> LENGTH: 21
<212> TYPE: DNA
<213> ORGANISM: Artificial Sequence
<220> FEATURE:
<223> OTHER INFORMATION: UQCRH rev primer

<400> SEQUENCE: 14
caaatggtac atccaaaacc a                                             21

<210> SEQ ID NO 15
<211> LENGTH: 22
<212> TYPE: DNA
<213> ORGANISM: Artificial Sequence
<220> FEATURE:
<223> OTHER INFORMATION: UQCRB fwd primer

<400> SEQUENCE: 15
gaaagagaag aatgggcaaa ga                                            22

<210> SEQ ID NO 16
<211> LENGTH: 22
<212> TYPE: DNA
<213> ORGANISM: Artificial Sequence
<220> FEATURE:
<223> OTHER INFORMATION: UQCRB rev primer

<400> SEQUENCE: 16
gaattcaaaa actccagcca tt                                            22

<210> SEQ ID NO 17
<211> LENGTH: 26
<212> TYPE: DNA
<213> ORGANISM: Artificial Sequence
<220> FEATURE:
<223> OTHER INFORMATION: UQCRB -351 bp ChIP fwd primer

<400> SEQUENCE: 17
cttcctgcct ggcacaaaga gctgaa                                        26

<210> SEQ ID NO 18
<211> LENGTH: 32
<212> TYPE: DNA
<213> ORGANISM: Artificial Sequence
<220> FEATURE:
<223> OTHER INFORMATION: UQCRB -351 bp ChIP rev primer

<400> SEQUENCE: 18
gggaagaaca caggtcagga attaggagac ca                                 32

<210> SEQ ID NO 19
<211> LENGTH: 36

<212> TYPE: DNA
<213> ORGANISM: Artificial Sequence
<220> FEATURE:
<223> OTHER INFORMATION: UQCRB -1,728 bp ChIP fwd primer

<400> SEQUENCE: 19
ccagtaacta tcagtcatgc tagctccccc taattg                        36

<210> SEQ ID NO 20
<211> LENGTH: 24
<212> TYPE: DNA
<213> ORGANISM: Artificial Sequence
<220> FEATURE:
<223> OTHER INFORMATION: UQCRB -1,728 bp ChIP rev primer

<400> SEQUENCE: 20
tccacccacg tcagcctccc aaaa                                     24

<210> SEQ ID NO 21
<211> LENGTH: 20
<212> TYPE: DNA
<213> ORGANISM: Artificial Sequence
<220> FEATURE:
<223> OTHER INFORMATION: mitochondrial transfer RNA-Leu (URR) fwd primer

<400> SEQUENCE: 21
cacccaagaa cagggtttgt                                          20

<210> SEQ ID NO 22
<211> LENGTH: 20
<212> TYPE: DNA
<213> ORGANISM: Artificial Sequence
<220> FEATURE:
<223> OTHER INFORMATION: mitochondrial transfer RNA-Leu (URR) rev primer

<400> SEQUENCE: 22
tggccatggg tatgttgtta                                          20

<210> SEQ ID NO 23
<211> LENGTH: 25
<212> TYPE: DNA
<213> ORGANISM: Artificial Sequence
<220> FEATURE:
<223> OTHER INFORMATION: B2M fwd primer

<400> SEQUENCE: 23
tgctgtctcc atgtttgatg tatct                                    25

<210> SEQ ID NO 24
<211> LENGTH: 22
<212> TYPE: DNA
<213> ORGANISM: Artificial Sequence
<220> FEATURE:
<223> OTHER INFORMATION: B2M rev primer

<400> SEQUENCE: 24
tctctgctcc ccacctctaa gt                                       22

<210> SEQ ID NO 25
<211> LENGTH: 510
<212> TYPE: DNA
<213> ORGANISM: Homo sapiens

<400> SEQUENCE: 25
aggaagagat aggtcatcaa acctttctg aaactacaat ttctccaata ttttcaactc    60

```
gaaataatca atgtaccaat tccatatatt tttgggatgg cacatccatc agtccttcaa    120
tagaaagtaa gacgatgccc ttaaaacatt tagcttcctg cctggcacaa agagctgaat    180
taatactgtc cacgctccca tagctattaa cagcaaataa cagaacccag ctttaagcct    240
tggtctccta attcctgacc tgtgttcttc ccatcacatc acaaccaata cttcttagaa    300
tgtagcacgc aaaatgcccc gcctactcca ttggcctcac cctggccgag aggtgcttac    360
gcaggtgctg aacggcagtc gtcagaactg cgcctgcgca agcggccttt ctctgttcgc    420
gatgtgacgt aacgcgcctg cggactgggc ccagcttgtc ctctatgact tacccagaag    480
gcaacgcttc tctttctggt caaaatggct                                     510

<210> SEQ ID NO 26
<211> LENGTH: 7
<212> TYPE: PRT
<213> ORGANISM: Artificial Sequence
<220> FEATURE:
<223> OTHER INFORMATION: RNA polymerase II CTD repeat sequence

<400> SEQUENCE: 26

Tyr Ser Pro Thr Ser Pro Ser
1               5
```

MANIPULATING ARID5B EXPRESSION IN IMMUNE CELLS TO PROMOTE METABOLISM, SURVIVAL, AND FUNCTION

CROSS-REFERENCE TO RELATED APPLICATIONS

This application is a U.S. National Stage of PCT Application No. PCT/US2019/031296 filed on May 8, 2019 which claims the benefit of priority to U.S. Provisional Patent Application Ser. No. 62/670,962, filed on May 14, 2018, which is herein incorporated by reference in its entirety.

STATEMENT REGARDING FEDERALLY SPONSORED RESEARCH OR DEVELOPMENT

This invention was made with government support under CA111412, HL122216, CA065493, and CA197292 awarded by National Institutes of Health. The government has certain rights in the invention.

BACKGROUND

Human natural killer (NK) cells are a subset of peripheral blood lymphocytes characterized by the absence of CD3/TCR expression and by the expression of CD16 and CD56 surface antigens. Unlike T cells and B cells, NK cells do not express rearranged, antigen-specific receptors. Instead, NK effector function (e.g., cytotoxicity, cytokine release) is dictated by the integration of signals received through germ-line-encoded receptors that can recognize ligands on their cellular targets. NK cells sense and kill target cells that lack major histocompatibility complex (MHC)-class I molecules, and are activated via NK cell activating receptors, the ligands of which are expressed on stressed, transformed, or infected cells but not on normal cells. In this manner, "normal" cells are resistant to NK cell killing.

Because NK cells directly kill tumor cells through several mechanisms and produce cytokines that can exert regulatory control of downstream adaptive immune responses, NK cells are ideal effector cells for therapeutic applications including anti-cancer therapies. Despite reports of clinical efficacy, a number of factors limit the application of natural killer (NK) cell immunotherapy for the treatment of cancer, such as the failure of infused NK cells to expand and persist in vivo. NK cells are innate lymphocytes with an estimated half-life of approximately 10 days. The short life span of NK cells presents a challenge in the field of immunotherapy, where lack of NK cell persistence is associated with higher rates of relapse. Studies by the inventors and others have shown that particular subsets of "adaptive" NK cells that arise in response to human cytomegalovirus infection appear to persist at stable frequencies for months and perhaps years. To further improve NK cell persistence for immunotherapies, conventional strategies have included transgenic expression of an IL-12/IL-15R construct. While this approach has the potential to promote NK cell persistence, studies have failed to demonstrate metabolic or functional changes in such transgenic cells to suggest improved anti-tumor efficacy. Accordingly, there remains a need in the art for methods of improving NK cell function and persistence, particularly for clinical immunotherapy applications.

SUMMARY

The present invention overcomes the aforementioned drawbacks by providing methods of manipulating ARID5B expression in NK cells, NK cell lines, and NK precursors to enhance their persistence and function in vivo. Also provided herein are modified NK cells and compositions comprising such modified cells for anti-cancer and other immunotherapies. In some embodiments, NK cells are genetically modified to increase ARID5B expression and, thus, increase improve anti-tumor efficacy.

In a first aspect, provided herein is an isolated population of modified immune cells having increased expression in AT-rich interaction domain 5B (ARID5B) relative to a wild-type immune cell, wherein the modified immune cells exhibit one or more of increased persistence, an increased level of glycolysis, and increased mitochondrial oxidative metabolism. The modified immune cells can comprise T cells, Natural Killer (NK) cells, or NKT (Natural Killer T) cells. The NK cell can be a primary NK cell or a NK-92 cell. The NK cell can be $CD3^-$, $TCR^-$, $CD56^+$, and $NKp46^+$. The modified immune cells can be differentiated in vitro from stem cells, hematopoietic stem or progenitor cells, or progenitor cells. The progenitor cell can be a CD34+ hemogenic endothelium cell, a multipotent progenitor cell, a T cell progenitor cell, a NK progenitor cell, or a NKT progenitor cell. The modified immune cells can comprise at least one genetically modified modality. The genetically modified modality can comprise a recombinant nucleic acid encoding an ARID5B polypeptide and operably linked to a heterologous promoter. The genetically modified modality can comprise a nucleic acid encoding a T-cell receptor (TCR) or a chimeric antigen receptor (CAR). The modified immune cells can be produced in vitro or ex vivo from immune cells isolated from or comprised in peripheral blood, bone marrow, lymph node tissue, cord blood, thymus tissue, tissue from a site of infection, ascites, pleural effusion, spleen tissue, or tumors. The modified immune cells can be produced in vitro or ex vivo by contacting immune cells to one or more agents that increase ARID5B gene expression in the cells compared to an immune cell that has not been contacted ex vivo with one or more agents that increase ARID5B gene expression. The immune cells can be isolated from or comprised in peripheral blood, bone marrow, lymph node tissue, cord blood, thymus tissue, tissue from a site of infection, ascites, pleural effusion, spleen tissue, or tumors.

In another aspect, provided herein is a cell composition comprising the population of modified immune cells as described herein and an acceptable carrier or excipient.

Also provided herein is a pharmaceutical composition comprising the population of modified immune cells as described herein and a pharmaceutically acceptable carrier or excipient.

In a further aspect, provided herein is a therapeutic composition for treating a tumor in a patient comprising the population of modified immune cells as described herein, wherein the modified immune cells are suspended in a medium suitable for injection.

In another aspect, provided herein is method of treating a subject in need of an adoptive cell therapy, the method comprising administering a therapeutically sufficient amount of a therapeutic composition provided herein to the subject. The subject can have cancer, a solid tumor, an autoimmune disorder; a hematological malignancy; or an infection associated with HIV, RSV, EBV, CMV, adenovirus, or BK polyomavirus. The subject can have breast cancer, ovarian cancer, brain cancer, prostate cancer, lung cancer, colon cancer, skin cancer, liver cancer, pancreatic cancer, or sarcoma. In some cases, the subject has received bone marrow ablative or non-myeolablative chemotherapy or radiation therapy. The subject can be a bone marrow donor. The cell therapy can be allogeneic.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

BRIEF DESCRIPTION OF THE DRAWINGS

The present invention will be better understood and features, aspects, and advantages other than those set forth above will become apparent when consideration is given to the following detailed description thereof. Such detailed description makes reference to the following drawings, wherein:

FIGS. 2A-2G demonstrate that adaptive NK cells have higher mitochondrial membrane potential and expression of ETC genes relative to canonical NK cells. (A) Representative FACS plots of CD57 and NKG2C expression on gated NK cells from HCMV-seronegative and HCMV-seropositive donors. (B) Representative histogram plots of MitoTracker staining within the indicated NK cell subsets (left panel) and cumulative data of MitoTracker mean fluorescence intensity (MFI) from 5 HCMV seronegative donors and 5 HCMV seropositive donors are shown (right panel). (C) Canonical and adaptive NK cells were sorted from PBMCs isolated from two HCMV-seropositive donors in two independent experiments, stained with MitoTracker and DAPI dyes and analyzed by confocal microscopy. Shown are representative images from one donor (left panel) and cumulative MitoTracker intensity values from 18 canonical NK cells and 20 adaptive NK cells (right panel). (D) Quantitative RT-PCR was used to determine the ratio of mitochondrial DNA to genomic DNA for canonical and adaptive NK cells. This ratio for adaptive NK cells is normalized against conventional NK cells to determine fold difference. Results are from four donors in two independent experiments. (E) Representative FACS histogram plots of CellRox staining in the indicated subsets of NK cells from a HCMV-seropositive donor (left panel) and cumulative data of CellRox MFI values from six donors in two independent experiments (right panel). (F) The indicated subsets of canonical and adaptive NK cells were sorted from PBMCs isolated from five HCMV-seropositive donors in three independent experiments and used for RNA-seq analysis. Shown is a heat map of normalized fold-expression values for mitochondrial ATP synthase complex and electron transport chain (ETC) genes in canonical and adaptive NK cells. (G) The indicated subsets of canonical and adaptive NK cells were sorted from PBMCs isolated from four HCMV-seropositive donors in two independent experiments and used for qRT-PCR. All expression values were normalized against ACTB and against gene expression values from CD3$^-$CD56$^{dim}$CD57$^-$NKG2C$^-$ canonical NK cells. Error bars represent S.E.M. Paired Student's t tests were used to determine statistical significance, *$p<0.05$, **$p<0.01$. n.s., not significant.

FIG. 13 is a table presenting GSEA of metabolic pathways that show differences between canonical and adaptive NK cells. Pathway analyses using RNA-seq data from CD3-CD56dimCD57+NKG2C− canonical NK cells and CD3-CD56dimCD57+NKG2C-adaptive NK cells were performed. Shown are gene sets for metabolic pathways that were significantly (or close to significantly) different between canonical and adaptive NK cells.

DETAILED DESCRIPTION

Figures 1A, 1B, 1C, 1D, 1E, 1F, 1G, 1H, 1I:
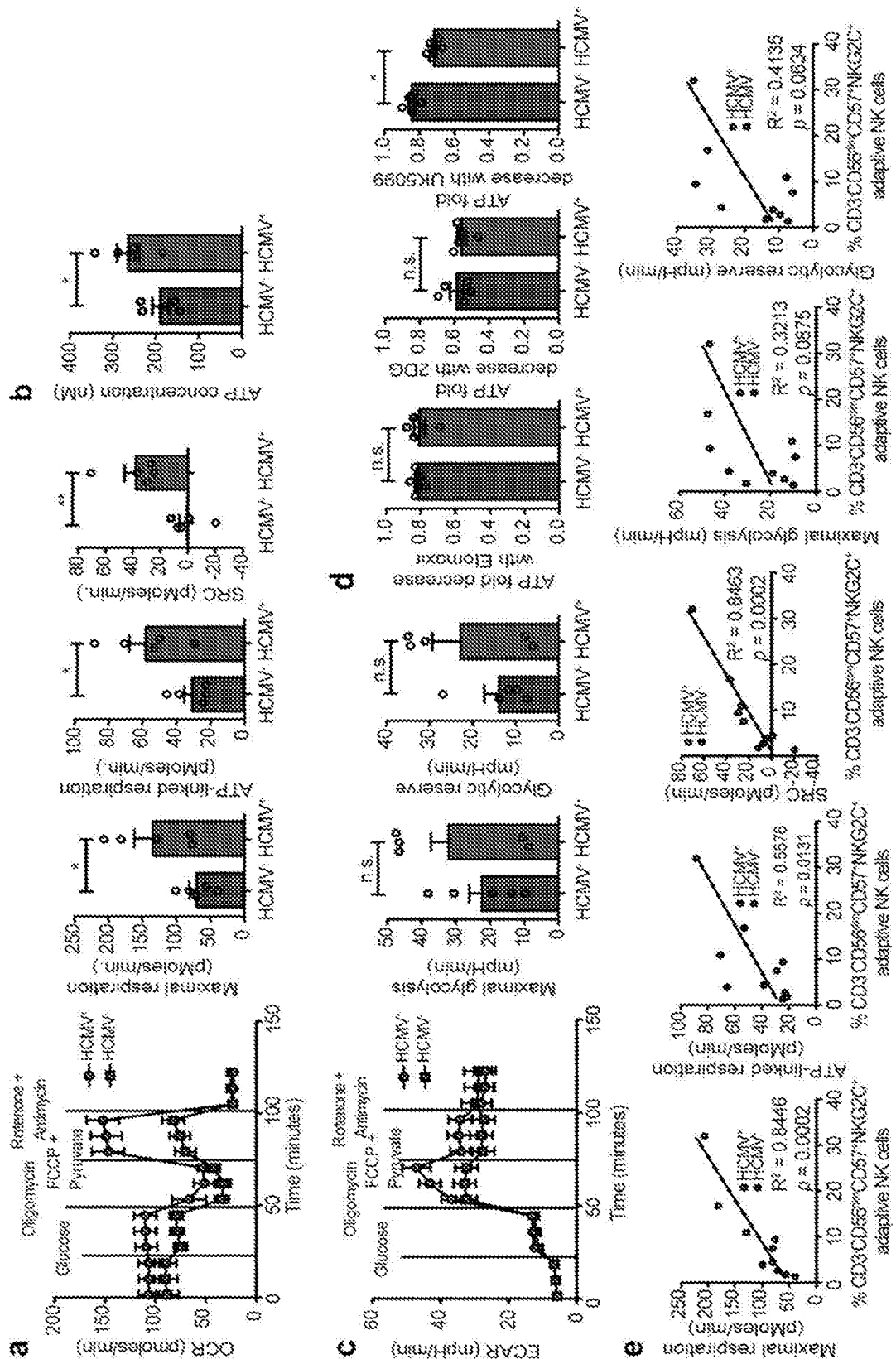
FIGS. 1A-1I demonstrate that adaptive NK cells exhibit higher glycolysis and mitochondrial oxidative metabolism relative to canonical NK cells. (a) Metabolic functions in freshly isolated NK cells from five HCMV-seropositive and five HCMV-seronegative donors were analyzed by Seahorse. Shown are OCR profiles for representative donors and averages for maximal respiration, ATP-linked respiration, and SRC. (b) Quantification of ATP in NK cells from four seronegative and four seropositive donors. (c) ECAR profiles for representative donors and averages for maximal glycolysis and glycolytic reserve. (d) NK cells were isolated from five seronegative and five seropositive donors and incubated with the indicated inhibitors for 10 min before lysis and ATP quantification. Shown are fold decreases in ATP for each inhibitor relative to vehicle controls. (a-d) Results are from two independent experiments. (e) Associations between Seahorse metabolic readouts and the percentages of adaptive NK cells. Unpaired Student's t tests were used to determine statistical significance. (f) Adaptive and canonical NK cells from three seropositive donors were sorted and analyzed by Seahorse. Shown is the OCR profile from a representative donor and averages for maximal respiration, ATP-linked respiration, and SRC. (g) Shown is the ECAR profile of canonical and adaptive NK cells from a representative donor, as well as the averages for maximal glycolysis and glycolytic reserve. All OCR and ECAR results are from two independent experiments. (h) Quantification of ATP in sorted canonical NK cells and adaptive NK cells from five seropositive donors. (i) Measurement of glucose uptake using 2-NBDG in isolated NK cells from six seropositive donors at rest, after stimulation with an anti-CD16 antibody and after stimulation with PMA: ionomycin. Shown are the 2-NBDG mean fluorescence intensity (MFI) averages in gated canonical and adaptive NK cells in each condition. Results are from two independent experiments. Paired Student's t tests were used to determine statistical significance. Error bars represent SEM. *$p<0.05$, **$p<0.01$. n.s., not significant.

The compositions and methods provided herein are based, at least in part, on the inventors' development of ways to promote mitochondrial metabolism in Natural Killer (NK) cells and NK precursors as a means to improve in vivo survival and function. Unlike prior, unsuccessful attempts to improve NK cell function by introducing IL-15/IL-15R transgenes, the inventors determined that increased levels of ARID5B (AT-rich interactive domain-containing protein 5B) improve NK cell survival, mitochondrial metabolism, and in vivo function. Accordingly, provided herein are NK cells modified for increased ARID5B expression, methods of increasing NK cell persistence and function, and improved immunotherapies in which NK cells modified as described herein are administered to a subject in need thereof.

Accordingly, provided herein are human immune cells (e.g., NK cells, T cells, NK T cells, other myeloid or lymphoid suppressor cells) and immune precursor cells (e.g., NK cell progenitors, T cell progenitors) modified for increased expression of ARID5B (AT-rich interactive domain-containing protein 5B). The term "modified" as used herein with respect to modified cells refers to an engineered cell in which expression of a target protein or nucleic acid is modulated (e.g., increased, decreased). In some cases, the immune cell is modified for increased expression of a human ARID5B gene. In some cases, the immune cell is genetically modified. In other cases, the immune cell is modified by virtue of exposure or contacting to an agent (e.g., protein, cytokine, small molecule) that upregulates expression of ARID5B by means other than genetic modification.

In some embodiments, the modified immune cell is a genetically engineered natural killer (NK) cell or natural killer cell progenitor, where the genetic modification increases AT-rich interaction domain 5B (ARID5B) gene expression or protein expression in the modified NK cell or NK cell progenitor relative to that of a wild-type NK cell or NK cell progenitor. As demonstrated in the Examples that follow, increased expression of ARID5B is associated with increased NK cell persistence, increased glycolysis, and increased mitochondrial oxidative metabolism relative to a wild-type NK cell or an NK cell not comprising the above-described genetic modification. Preferably, genetically engineered natural killer (NK) cell and NK precursor cells exhibit increased persistence relative to wild-type NK cells or NK cells not modified in the same manner. As used herein, the term "persistence" refers to capacity of cells to establish a stable, viable cell population that can be expanded in vivo or ex vivo, preferably for more than 7 days. One of the barriers of allogeneic cell therapy is that the infused cells are rejected by the patient. Retention of infused cells for 7-14 days or longer correlates with improved patient outcomes. Conventional methods to improve NK cell persistence involve cytotoxic lymphodepletion therapies. Without being bound to any particular theory or mode of action, it is believed that ARID5B expression in NK cells may contribute to overcoming this barrier.

As used herein, "gene expression" refers to the relative levels of expression and/or pattern of expression of a gene in a biological sample, such as immune cells, or population of cells comprising immune cells. In particular embodiments, the immune cells are NK cells, NK cell progenitors, T cells, or hematopoietic stem or progenitor cells. The expression of a gene, such as ARID5B, may be measured at the level of cDNA, RNA, mRNA, or combinations thereof. In some cases, increased expression of ARID5B is measured at the level of ARID5B protein. In some cases, the level of ARID5B gene expression or ARID5B protein expression is multiple fold (e.g., 2, 3, 4, 5, 10, 20, 50, 100) higher than in wild-type immune cells or immune cells not modified as described herein.

As used herein, "NK cells" means cytotoxic effector cells with the capacity to lyse tissue culture cells without participation of an antibody and without in vitro or in vivo sensitization. NK cells may also be characterized by the presence of cell surface receptors or proteins that distinguish NK cells from other lymphoid cells, and cells of the erythroid or myeloid lineages, for example, see, Bradshaw et al., Handbook of Cell Signaling (2003). Exemplary NK cells are primary NK cells or cells of a NK cell line (e.g., NK-92 cells). In some cases, the NK cells are adaptive NK cells. Human natural kill precursor cells and human NK cells are CD56+ (CD56-positive), and can be positive for expression for one or both of CD16 and NKp46, and lack a TCR complex and, thus, are CD3 negative. In some cases, NK cells have the following expression profile: CD3−, TCR−, CD56+, NKp46+. NK cells may additionally be characterized by one or more of the following: NK1.1+, CD3−, TCRαβ−, TCRδγ−, CD4−, CD8−, CD19−, CD25+, CD43+, CD45+, CD49b−, CD51+, CD94+, NKG2D+, Mac-1−/low, B220−, c-kit+, perforin I+, granzyme B+, and Notch-1+. As used herein, the terms "NK cell progenitor" and "NK precursor cell" are used interchangeably herein and refer to cells capable of differentiation into NK cells and encompasses hematopoietic stem cells (HSCs) that differentiate into NK cells, when Jagged2, Flt3L, IL-7, and SCF are expressed in co-cultured cells or added to the growth media. Optionally, IL-2 may be supplied. Cells useful for the compositions and methods provided herein can be freshly isolated primary cells or obtained from a frozen aliquot of a primary cell culture. NK precursor cells can be obtained from blood, bone marrow, cord blood, cell lines, or from differentiation of pluripotent stem cells (e.g., induced pluripotent stem cells (iPS) cells, embryonic stem cells).

In some embodiments, the immune cell is modified by virtue of exposure or contacting to an agent (e.g., protein, cytokine, small molecule) that upregulates expression of ARID5B by means other than genetic modification.

In some embodiments, the modified immune cell is a genetically engineered T cell, where the genetic modification increases expression of an ARID5B gene product or polypeptide in the modified T cell relative to a wild-type T cell. T cells appropriate for use according to the methods provided herein include mononuclear cells obtained from human blood and include, without limitation, peripheral blood mononuclear cells (PBMCs), also known as peripheral blood mononuclear lymphocytes (PBLs), bone marrow-derived mononuclear cells, and cord blood mononuclear cells (CBMCs). In some cases, T cells are obtained from biological samples comprising lymph node tissue, bone marrow, and/or splenocytes. Any appropriate method of isolating T cells from a biological sample of a subject can be employed. For example, T cells can be isolated, separated, or otherwise removed from the blood or a leukocyte milieu (e.g., obtained by leukapheresis), whereby isolated or separated T cells exist in a physical milieu distinct from that in which they occur in vivo. The term "isolated" does not imply any particular degree of purity, and the absolute level of purity is not critical. Those skilled in the art can readily determine appropriate levels of purity for use according to the methods provided herein. Those skilled in the art are familiar with many established protocols for isolating PBMCs. Human peripheral blood may be drawn conveniently via venipuncture. Isolation of PBMCs can be aided by density-gradient separation protocols, usually employing a density-gradient centrifugation technique such as Ficoll®-Hypaque or Histopaque® for separating lymphocytes from other formed elements in the blood. Preferably, PBMC isolation is performed under sterile conditions. Alternatively, cell elutriation methods may be employed to separate mononuclear cell populations. Advantages of the cell elutriation method include sterility and efficiency.

As used herein, the terms "genetically modified" and "genetically engineered" are used interchangeably and refer to a prokaryotic or eukaryotic cell that includes an exogenous polynucleotide, regardless of the method used for insertion. In some cases, a natural killer cell or NK cell precursor has been modified to comprise a non-naturally occurring nucleic acid molecule that has been created or modified by the hand of man (e.g., using recombinant DNA technology) or is derived from such a molecule (e.g., by transcription, translation, etc.). An effector cell that contains an exogenous, recombinant, synthetic, and/or otherwise modified polynucleotide is considered to be an engineered cell. In some cases, modified cells contain one or more recombinant nucleic acids. In other cases, modified cells contain one or more synthetic or genetically engineered nucleic acids (e.g., a nucleic acid containing at least one artificially created insertion, deletion, inversion, or substitution relative to the sequence found in its naturally occurring counterpart). A cell comprising one or more exogenous, recombinant, synthetic, and/or otherwise modified nucleic acids is considered to be a genetically engineered cell and, thus, non-naturally occurring relative to any naturally occurring counterpart. Procedures for producing genetically engineered cells are generally known in the art, and are described in Sambrook et al, *Molecular Cloning, A Laboratory Manual*, Cold Spring Harbor Press, Cold Spring Harbor, N.Y. (1989), incorporated herein by reference.

Immune cells and immune cell progenitors may be genetically engineered either in vivo, in vitro, or ex vivo, for example, reporter constructs may be introduced, or recombinant nucleic acids or therapeutic gene products may by introduced or alternatively regulated. In some cases, cells are modified by introducing (e.g., achieving uptake of nucleic acids by transduction, transfection, electroporation, etc.) recombinant nucleic acids or therapeutic gene products. In other cases, cells are modified by introducing mutations into genes of the cells. Insertion or deletion mutations may be introduced in a cell using standard techniques. A nucleic acid encoding a selectable marker may also be introduced into the cells. In some cases, genetically modified cells are cultured in vitro under suitable conditions so that they are able to express the product of the gene expression or secrete the expression product.

Those skilled in the field of molecular biology will understand that any of a wide variety of expression systems may be used to provide a recombinant protein or protein fragment. The methods of transformation, transfection or transduction, and the choice of expression vector will depend on the host system, desired stability and/or availability of appropriate restriction endonuclease sites. Transformation and transfection methods are described, e.g., in Ausubel, et al., 1997, expression vectors may be chosen from those provided, for example, in Pouwels et al., 1985, Supp. 1987, or known in the art.

In some cases, genetically modified immune cells (e.g., NK cells, T cells, NK precursor cells) are produced by introducing a recombinant nucleic acid encoding an ARID5B polypeptide. The recombinant nucleic acid can encode human ARID5B polypeptide, variant 1 (NCBI accession number NM_032199.2) or human ARID5B polypeptide, variant 2 (NCBI accession number NM_001244638.1). In some cases, the cell is genetically modified such that the resulting modified cell comprises an exogenous nucleic acid molecule encoding ARID5B. For example, in some cases, NK cells are stably transfected with an expression vector comprising a nucleic acid molecule encoding human ARID5B, whereby the resulting transfected cells express exogenous ARID5B polypeptide. In some cases, the exogenous nucleic acid is operably linked to a heterologous promoter. In one embodiment, ARID5B overexpression is achieved using an inducible expression system.

Moreover, ARID5B genes from other species that have a polynucleotide sequence that differs from a sequence encoding a human ARID5B polypeptide are contemplated to be useful in the compositions and methods of the invention. In some cases, genetically modified immune cells (e.g., NK cells, T cells, NK precursor cells) express an ARID5B variant polynucleotide. The terms "ARID5B variant polynucleotide" or "ARID5B variant polynucleotide sequence" means a polynucleotide molecule which encodes an ARID5B polypeptide that (1) has at least about 70% polynucleotide sequence identity with a polynucleotide acid sequence encoding a full-length native ARID5B or any other fragment of a full-length ARID5B. Ordinarily, a ARID5B variant polynucleotide will have at least about 70% polynucleotide sequence identity, more preferably at least about 71%-99% polynucleotide sequence identity and yet more preferably at least about 75%, 80%, 85%, 90%, 91%, 92%, 93%, 94%, 95%, 96%, 97%, 98% and even more preferably, 99% polynucleotide sequence identity with the polynucleotide sequence encoding a full-length, native ARID5B.

"Percent (%) polynucleotide sequence identity" with respect to ARID5B-encoding polynucleotide sequences is defined as the percentage of polynucleotides in the ARID5B polynucleotide sequence of interest that are identical with the polynucleotides in a candidate sequence, after aligning the sequences and introducing gaps, if necessary, to achieve the maximum percent sequence identity. Alignment can be achieved in various ways well-known in the art; for instance, using publicly available software such as BLAST, BLAST-2, ALIGN or Megalign (DNASTAR) software. Techniques and software for determining sequence homology or identity between two or more amino acid or nucleic acid sequences are well known in the art. Homologs, orthologues, and paralogs can be identified using PCR, for example, using targeted degenerate primers to amplify nucleic acid sequences which may encode for the corresponding conserved amino acid sequences. In addition, homologs, orthologues, and paralogs may be identified by sequence alignment using sequence databases, e.g., expressed sequence tag (EST) databases.

Constructs of the invention used to express human ARID5B or other mammalian ARID5B homologs, orthologues, and/or paralogs may be prepared for introduction into an immune cell (e.g., NK cells, T cells, NK precursor cells) or, in the case of a NK precursor cell, a HSC and may comprise a replication system recognized by the host, and will preferably also include transcriptional and translational regulatory sequences operably linked to the nucleotide sequence encoding ARID5B. The vector may be an autonomously replicating vector, a viral or phage vector, a transposable element, an integrating vector or an extrachromosomal element, such as a minichromosome or an artificial chromosome. Such vectors may be prepared by means of standard recombinant techniques well known in the art. See, for example, Ausubel et al., 1992, Sambrook et al., 2001, and U.S. Pat. No. 5,837,492. As used herein, the term "vector" refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Encompassed by the term "vector" is exogenous genetic material that allow for the expression of a transgene.

In some cases, it will be advantageous to further genetically modify a cell using the methods described herein such that the genetically engineered immune cell (e.g., NK cell, T cell, NK precursor cell) comprises one or more additional genetic modifications. For example, a genetically engineered immune cell may further comprise one or more additional transgenes for expression of an exogenous nucleic acid. Additionally or alternatively, the genetically engineered immune cell may further comprise a genetic mutation that knocks out expression of a particular gene product.

In some cases, the genetically engineered immune cell (e.g., NK cell, T cell, NK precursor cell) is further modified to comprise an exogenous nucleic acid that encodes an immune receptor (e.g., a recombinant immune receptor, a mutated or non-naturally occurring immune receptor). In some cases, the exogenous nucleic acid encodes a T cell receptor (TCR). For example, in some cases it may be advantageous to modify immune cells to express an antigen-specific T cell receptors that recognize tumor peptides and MHC. In other cases, the exogenous nucleic acid encodes a chimeric antigen receptor (CAR). As used herein, the term "chimeric antigen receptor (CAR)" refers to an artificially constructed hybrid protein or polypeptide comprising an extracellular antigen binding domains of an antibody (e.g., single chain variable fragment (scFv)) operably linked to a transmembrane domain and at least one intracellular domain. The "chimeric antigen receptor (CAR)" is sometimes referred to as a "chimeric receptor" or a "chimeric immune receptor (CIR)." Generally, the antigen binding domain of a CAR has specificity for a particular antigen expressed on the surface of a target cell of interest. For example, for anti-tumor cell therapeutics, cells can be engineered to knock-in nucleic acids encoding a CAR having specificity for, for example, tumor-specific surface antigens.

In some cases, it may be advantageous to obtain immune cells having the genetic complement of a particular human subject. For example, it may be advantageous to obtain immune cells that exhibit one or more specific phenotypes associated with or resulting from a particular disease or disorder of the particular mammalian subject. In such cases, human induced pluripotent stem (iPS) cells are obtained by reprogramming a somatic cell of a particular human subject according to methods known in the art. See, for example, Yu et al., *Science* 324(5928):797-801 (2009); Chen et al., *Nat. Methods* 8(5):424-9 (2011); Ebert et al., *Nature* 457(7227): 277-80 (2009); Howden et al., *Proc. Natl. Acad. Sci. U S. A.* 108(16):6537-42 (2011). In some cases, it will be advantageous to obtain iPS cells from a subject and subsequently induce the subject-specific iPS cells to assume a definitive hematopoietic phenotype, such as, for example, T cells, B cells, NKT cells, or NK cells.

As used herein, "induced pluripotent stem cells" or "iPS cells" mean a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to higher potency cells, such as embryonic stem cells. See, e.g., Yu et al., *Science* 318: 1917-1920 (2007).

Subject-specific somatic cells for reprogramming into iPS cells can be obtained or isolated from a target tissue of interest by biopsy or other tissue sampling methods. In some cases, subject-specific cells are manipulated in vitro prior to somatic cell reprogramming. For example, subject-specific cells can be expanded, differentiated, genetically modified, contacted to polypeptides, nucleic acids, or other factors, cryo-preserved, or otherwise modified prior to somatic cell reprogramming.

In some cases, iPS cells are modified to overexpress ARID5B relative to unmodified iPS cells and are subsequently differentiated in vitro to obtain cells of the hematopoietic-derived lineages such as NK cells, T cells (e.g., Tregs), myeloid-derived suppressor cells (MDSCs), NK precursor cells, dendritic cells, anti-tumor monocytes, and any other any hematopoietic cell-derived cell type. Any appropriate in vitro method of directing differentiation of iPS cells, modified to overexpress ARID5B as described herein, can be used to obtain cells of the hematopoietic-derived lineages. For example, in vitro methods for deriving NK cells from iPS cells have been previously described. See, e.g., Knorr et al., *Stem Cells Transl Med* (2013); 2:274-283; Ng et al., *Nat Protoc* 2008; 3:768-776.

In another aspect, provided herein is a cell composition, such as a pharmaceutical composition, comprising a plurality of the genetically engineered immune cells (e.g., NK cells, T cells, NK precursor cells) described herein and an acceptable carrier, diluents, or excipient (e.g., a pharmaceutically acceptable carrier, diluent, excipient or a combination thereof). The means of making such a composition have been described in the art (see, for instance, Remington's Pharmaceutical Sciences, 16th Ed., Mack, ed. (1980)). Preferably, the composition is prepared to facilitate the administration of the cells into a living organism. In some cases, the pharmaceutical composition comprises a plurality of genetically engineered effector cells as described herein and, for example, a balanced salt solution, preferably Hanks' balanced salt solution, or normal saline. In some cases, the cell composition is a therapeutic composition for treating a tumor in a subject. In such cases, a plurality of genetically engineered cells of this disclosure are suspended in a medium suitable for administration (e.g., injection, infusion) to a subject in need of such treatment.

Cell preparations for use in clinical applications must be obtained in accordance with regulations imposed by governmental agencies such as the U.S. Food and Drug Administration. Accordingly, in exemplary embodiments, the methods provided herein are conducted in accordance with Good Manufacturing Practices (GMPs), Good Tissue Practices (GTPs), and Good Laboratory Practices (GLPs). Reagents comprising animal derived components are not used, and all reagents are purchased from sources that are GMP-compliant. In the context of clinical manufacturing of cell preparations for use in human therapies, GTPs govern cell donor consent, traceability, and infectious disease screening, whereas GMPs are relevant to the facility, processes, testing, and practices to produce consistently safe and effective products for human use. See Lu et al. *Stem Cells* 27: 2126-2135 (2009). Where appropriate, oversight of patient protocols by agencies and institutional panels is envisioned to ensure that informed consent is obtained; safety, bioactivity, appropriate dosage, and efficacy of products are studied in phases; results are statistically significant; and ethical guidelines are followed.

The genetically engineered cells and cell compositions provided herein having properties advantageous for use in a variety of in vitro, ex vivo, and in vivo applications. For example, in vitro uses of the cells and cell compositions provided herein include, without limitation, targeting diseased target cells on the basis of antigens expressed on the surface of the diseased target cells. The target cell can be a cancer cell (e.g., tumor cell), a cell infected by a pathogen such as a virus or bacterium, a cell type associated with an autoimmune disorder (e.g., Type 1 diabetes, lupus), or a cell type associated with a neurodegenerative disease such as Alzheimer's Disease, ALS, or Huntington's Disease. Also, the cell can be a cell type associated with any other pathology for which the affected cell having aberrant expression of a cell surface antigen relative to an unaffected cell.

In some cases, the genetically engineered cells and cell compositions provided herein exhibit advantageous properties following cryopreservation, storage at a sub-zero temperature, and thawing. As used herein, the term "cryopreservation" refers to preserving cells by cooling to a sub-zero temperature. In some cases, cryopreservation takes place in the presence or absence of a cryoprotective agent, which is a substance that protects cells from damage associated with storage at sub-zero temperature and/or freezing, e.g., cell membrane damage due to ice crystal formation. In some cases, cryopreserved and thawed modified cells of this disclosure exhibit improved viability and maintenance of function following cryopreservation and thawing relative to control cells that do not overexpress ARID5B. Without being bound by any particular theory or mode of action, it is believed that one or more metabolic changes that occur in a modified cell in response to overexpression of ARID5B improve the viability and the efficiency and maintenance of function of such cells after cryopreservation and thawing for use. For example, ARID5B is known to increase mitochondrial membrane potential and increase expression of BCL-2, both of which generally promote cell survival after the stress of freezing and thawing. See, e.g., Stroh et al., *The FASEB Journal* 2002, DOI 10.1096/fj.02-0034fje.

Ex vivo uses of the genetically engineered cells and cell compositions provided herein include, without limitation, early disease detection and companion diagnostic or therapeutic applications for the disease target cells identified on the basis of antigens expressed on the surface of the disease target cells. For example, the cells can be used for ex vivo applications in companion therapeutic for cancer immunotherapy. Other ex vivo applications of the genetically engineered cells and cell compositions of this disclosure include, without limitation, applications for companion diagnostics for cell therapies for treating infectious diseases, autoimmune disorders, neurodegenerative disorders, and other cell-based pathologies associated with aberrant expression of a cell surface antigen relative to an unaffected cell.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured in a laboratory apparatus, usually under sterile conditions, and typically for a few hours or up to about 24 hours, but including up to 48 or 72 hours or longer, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g, nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). Nucleic acids encompass polymers of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions. In some embodiments, the nucleic acid may encode additional amino acid sequences that do not affect the function of the CAR and polynucleotide and which may or may not be translated upon expression of the nucleic acid by a host cell.

Nucleic acids can be obtained using any suitable method, including those described by Maniatis et al., Molecular Cloning: A Laboratory Manual, Cold Spring Harbor, N.Y., pp. 280-281 (1982). In some aspects, nucleic acids are obtained as described in U.S. Patent Application Publication No. US2002/0190663. Nucleic acids obtained from biological samples typically are fragmented to produce suitable fragments for analysis.

Nucleic acids and/or other moieties of the invention may be isolated. As used herein, "isolated" means separate from at least some of the components with which it is usually associated whether it is derived from a naturally occurring source or made synthetically, in whole or in part. Nucleic acids and/or other moieties of the invention may be purified. As used herein, "purified" means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain and a nucleic acid cleavage domain. In some embodiments, a protein comprises a proteinaceous part, e.g., an amino acid sequence constituting a nucleic acid binding domain, and an organic compound, e.g., a compound that can act as a nucleic acid cleavage agent.

Methods

In another aspect, provided herein are methods of treating or preventing a disease using modified immune cells as provided herein as a therapeutic agent. In some cases, provided herein is a method of treating a disease (e.g., cancer, viral infection) in a subject in need thereof, where the method comprises administering to the subject modified immune cells having increased expression in ARID5B relative to a wild-type immune cell. As used herein, the terms "subject," "patient," and "individual" are used interchangeably and can encompass any vertebrate including, without limitation, humans, mammals, reptiles, amphibians, and fish. However, advantageously, the subject, patient, or individual is a mammal such as a human, or a mammal such as a domesticated mammal, e.g., dog, cat, horse, and the like, or livestock, e.g., cow, sheep, pig, and the like. In exemplary embodiments, the subject is a human.

In some cases, subjects for whom the methods provided herein are particularly suitable have received bone marrow ablative or non-myeolablative chemotherapy or radiation therapy. In other cases, the subject is a bone marrow donor.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of disease in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

As used herein, the phrase "in need thereof" indicates the state of the subject, wherein therapeutic or preventative measures are desirable. Such a state can include, but is not limited to, subjects having a disease or condition such as cancer or viral infection. In some cases, the subject has a cancer such as a hematological malignancy (e.g., acute leukemia, chronic leukemia (myeloid or lymphoid), lymphoma (Hodgkin's or non-Hodgkin's), multiple myeloma, myelodysplastic syndrome) or a non-hematological cancer such as solid tumors (including breast cancer, ovarian cancer, brain cancer, prostate cancer, lung cancer, colon cancer, skin cancer, liver cancer, sarcoma, or pancreatic cancer). Other subjects may have disorders caused by an infection (e.g., viral infection, bacterial infection or fungal infection). In some cases, the infection to be treated is one that causes damage to stem or progenitor cells of the bone marrow.

In some cases, the method comprises administering to a subject in need thereof modified immune cells (e.g., NK cell, T cell, NK precursor cell) having increased expression in ARID5B relative to a wild-type immune cell. As described herein, such modified immune cells exhibit one or more of increased mitochondrial membrane potential, increased IFN-γ production, whereby the administering to the individual treats the disease. As described herein, modified immune cells can be produced in vitro or ex vivo. Due to the enhanced properties of immune cells overexpressing or expressing exogenous ARID5B, such methods can increase the efficacy of conventional cell therapies, including increasing the number of patients that achieve remission and/or remain in remission following treatment according to the methods described herein.

In some cases, modified immune cells are administered to a subject in need thereof as a composition comprising the modified cells and a suitable carrier, diluent, or excipient as described herein. Any appropriate method of providing modified immune cells to a subject can be used for methods described herein. In some cases, methods for providing cells to a subject can be adapted from clinical protocols for cellular and adoptive immunotherapy for infusion of donor-derived immune cells into a human subject. In some cases, an adapted clinical protocol suitable for methods provided by the present invention comprises obtaining immune cells from a subject, modifying the immune cells as described herein, and infusing the modified cells back into the subject.

Administration of the modified immune cell compositions provided herein can be administered by any appropriate route, including, without limitation, administration intravenously, intratumorally, intramuscularly, subcutaneously, intraperitoneally, intra-arterially, or into an afferent lymph vessel, by parenteral administration, for example, by injection or infusion. The cells may be administered in a mixture with other cells or separately and may be delivered to a target area, e.g. by intratumoral injection, or the cells may be introduced intravenously and allowed to migrate to a target area.

For purposes of the inventive methods, where modified immune cells or populations of such modified cells are administered, the modified immune cells can be cells that are allogeneic or autologous to the subject (e.g., human patient).

In some cases, a subject to which modified immune cells are provided is monitored or assessed for increased (e.g., improved, more robust) tumor clearance. Accordingly, methods of the present invention are useful for cancer therapies. In some cases, a subject to which modified immune cells are provided is monitored or assessed for clearance of cells expressing a particular antigen.

Articles of Manufacture

In another aspect, provided herein is a kit for treating a subject in need of an adoptive cell therapy. Preferably, the kit comprises a therapeutic composition comprising modified immune cells having increased expression in ARID5B relative to a wild-type immune cell as described in this disclosure. In some cases, the modified immune cells are provided in a pharmaceutically acceptable medium suitable for injection. In some cases, the modified immune cells are provided as cryopreserved cells. In such cases, the kit may further comprise instructions for thawing the cryopreserved cells and/or for administering the therapeutic composition to the subject in need of adoptive cell therapy.

In another aspect, provided herein a kit for obtaining functional modified immune cells having increased expression in AT-rich interaction domain 5B (ARID5B) relative to a wild-type immune cell by genetically modifying and differentiating human pluripotent stem cells, such as induced pluripotent stem cells, preferably under chemically defined culture conditions.

Unless otherwise indicated, any nucleic acid sequences are written left to right in 5' to 3' orientation; amino acid sequences are written left to right in amino to carboxy orientation, respectively.

All references, including publications, patents, and patent applications, cited herein are hereby incorporated by reference to the same extent as if each reference were individually and specifically indicated to be incorporated by reference and were set forth in its entirety herein.

As used in this specification and the appended claims, the singular forms "a," "an," and "the" include plural references unless the context clearly dictates otherwise. Any reference to "or" herein is intended to encompass "and/or" unless otherwise stated.

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items.

As used herein, "about" means within 5% of a stated value (e.g., within a stated concentration range, within 5% of a stated time frame).

The invention will be more fully understood upon consideration of the following non-limiting examples.

EXAMPLES

Each publication, patent, and patent publication cited in this disclosure is incorporated in reference herein in its entirety. The present invention is not intended to be limited

Example 1—ARID5B Regulates Metabolic Programming in Human Adaptive NK Cells

The inventors' previous work demonstrated that natural killer (NK) cells having adaptive immunological properties expand and persist in response to human cytomegalovirus. This Example explores metabolic processes unique to these cells and demonstrates that adaptive $CD3^-CD56^{dim}CD57^+$ $NKG2C^+$ NK cells exhibit metabolic hallmarks of lymphocyte memory including increased oxidative mitochondrial respiration, mitochondrial membrane potential, and spare respiratory capacity. Mechanistically, it was determined that a short isoform of the chromatin-modifying, transcriptional regulator AT-rich interaction domain 5B (ARID5B) was selectively induced through DNA hypomethylation in adaptive NK cell. Knockdown of ARID5B in an NK cell line (NK-92) led to decreased mitochondrial oxidative metabolism, expression of ETC genes, survival, and IFN-γ production. Conversely, over-expression of ARID5B in NK-92 cells was associated with increased oxidative metabolism and IFN-γ production. Furthermore, it was further determined that ARID5B directly regulates expression of the ETC component ubiquinone-cytochrome c reductase-binding protein (UQCRB), and UQCRB knockdown phenocopied the metabolic and functional effects observed for ARID5B knockdown. Accordingly, these assays demonstrate an important role for ARID5B in regulating NK cell metabolism.

Results

Adaptive NK Cells From HCMV Seropositive Donors Exhibit Elevated Glycolytic and Oxidative Metabolism Relative to Canonical NK Cells To study how metabolism is regulated in NK cells that arise and persist in response to HCMV infection, we isolated $CD3^-CD56^+$ NK cells from the peripheral blood of HCMV seropositive and seronegative donors and measured $O_2$ consumption rates (OCR) at the basal state, after the addition of oligomycin (an inhibitor of ATP synthesis), FCCP (uncouples ATP synthesis from the electron transport chain, ETC), and rotenone and antimycin A, which interfere with complex I and complex III of the ETC, respectively (Gerencser et al., 2009)). We found that maximal respiration levels, ATP-linked respiration and SRC were significantly elevated in NK cells from HCMV seropositive donors (FIG. 1A). To determine whether observed increases in measures of OXPHOS were associated with the frequency of adaptive $CD3^-CD56^{dim}CD57^+NKG2C^+$ NK cells within the bulk $CD3^-CD56^+$ population, we phenotyped NK cells from all HCMV seropositive and seronegative donors tested. As expected, adaptive NK cells were present in HCMV seropositive donors at higher frequencies (7.5-32.1%) relative to seronegative donors (1.32-4.33%; $p=0.034$). Strong correlations were observed between the magnitude of maximal respiration, ATP-linked respiration, and SRC and the frequencies of adaptive NK cells (FIG. 1E).

As previously published, modifications of the Seahorse technology, adding glucose and pyruvate along with OXPHOS reagents in the same assay can maximize metabolic readouts from limited cell numbers (Marcais et al., 2014), was used to measure the extracellular acidification rate (ECAR) of primary NK cells as an indicator of glycolysis. No statistically significant differences were observed between NK cells from HCMV seropositive and seronegative donors with respect to maximal glycolysis and glycolytic reserve (FIG. 1C). Weaker correlations were evident between the magnitude of maximal glycolysis and glycolytic reserve and the frequencies of adaptive NK cells (FIG. 1E). We also observed higher ATP levels in NK cells from HCMV seropositive donors with adaptive NK cell expansions relative to NK cells from HCMV seronegative donors in direct ATP quantification assays (FIG. 1B).

To investigate which nutrient source supports the increase in ATP levels observed in NK cells from HCMV seropositive donors, pre-treated NK cells from HCMV seronegative and seropositive donors were treated with etomoxir (to block fatty acid transport into the mitochondria), 2DG (to block glycolysis) and UK5099 (to block pyruvate transport into the mitochondria) prior to ATP quantification. Etomoxir or 2DG did not affect observed reductions of ATP levels. However, UK5099 pre-treatment induced more substantial decreases in ATP production in NK cells from HCMV seropositive donors, suggesting that mitochondrial utilization of glucose plays a role in supporting the enhanced metabolism of adaptive NK cells (FIG. 1D).

Figure 9:
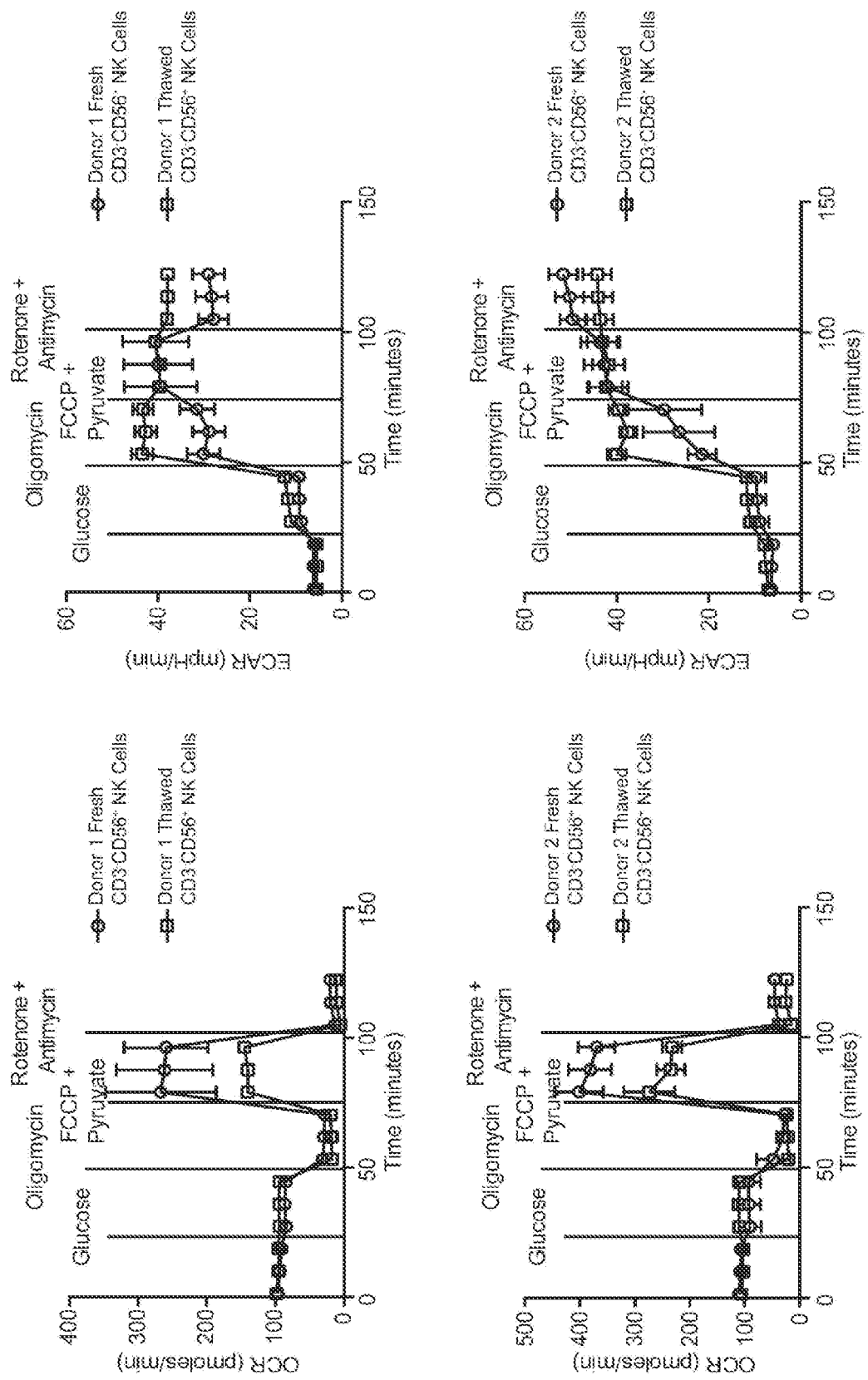
FIG. 9 demonstrates a comparison of OCR and ECAR profiles between fresh and previously frozen NK cells. PBMCs were isolated from whole blood from two healthy donors. $CD3^-CD56^+$ NK cells were isolated from a fraction of the PBMCs and used immediately for Seahorse analysis. The remaining PBMCs were frozen in liquid nitrogen using rate-controlled freezer. Three days later, cells were thawed and rested overnight. NK cells were then isolated and rested overnight before Seahorse analysis. Shown are the OCR and ECAR plots of fresh versus frozen NK cells from both donors. Error bars represent SEM.

To directly analyze metabolic responses in distinct NK cell subsets, we sorted peripheral blood canonical NK cells and adaptive NK cells from HCMV seropositive donors and performed Seahorse assays. In these experiments we observed markedly enhanced OCR profiles for adaptive NK cells with significant elevations in maximal respiration, ATP-linked respiration and SRC relative to canonical NK cells (FIG. 1F). Similarly, adaptive NK cells showed higher ECAR profiles with elevated maximal glycolysis and glycolytic reserve relative to canonical NK cells (FIG. 1G). Higher ATP levels were also observed in sorted adaptive NK cells relative to sorted canonical NK cells (FIG. 1H). To confirm the differences between isolated canonical and adaptive NK cells with respect to glycolytic metabolism, we performed glucose uptake assays using the fluorescent glucose analog 2-NBDG. We observed significantly more glucose uptake in adaptive NK cells in response to triggering through CD16 as well as activation using PMA:ionomycin (FIG. 1I). Of note, Seahorse experiments were either performed with freshly isolated NK cells or NK cells from PBMCs that had previously been frozen. In direct comparisons, though maximal respiration was lower in frozen cells, the overall OCR and ECAR profiles were similar (FIG. 9). Together, these data suggest that both mitochondrial oxidative metabolism and glycolysis are enhanced in adaptive NK cells from HCMV seropositive donors.

Adaptive NK Cells Display Increased Mitochondrial Membrane Potential and Expression of Genes Encoding Components of the Electron Transport Chain One of the most striking findings from our metabolic analyses was the dramatic increase in SRC in adaptive NK cells from HCMV seropositive donors. SRC is a measure of how efficiently the ETC can shuttle protons from the mitochondrial matrix into the intermembrane space in response to the ATP synthesis uncoupling agent FCCP relative to the basal state (Mookerjee et al., 2010) and is considered to be a reflection of the ability of cells to produce energy in response to increased work or stress (Nicholls, 2009). Elevated SRC is associated with increased mitochondrial mass and a memory phenotype in $CD8^+$ T cells (van der Windt et al., 2012, 2013). To determine whether differences in mitochondrial membrane potential were evident between subsets of canonical and adaptive NK cells, we isolated $CD3^{31}$ $CD56^+$ NK cells from HCMV seropositive and seronegative donors and stained with fluorescently-conjugated antibodies against CD57 and NKG2C for FACS analysis (FIG. 2A) along with MitoTracker Deep Red, a fluorescent cell-permeable dye that relies on mitochondrial membrane potential (Δψm) (Perry et al., 2011). We observed similar staining intensity in canonical CD3⁻CD56$^{dim}$NKG2C⁻ K cell subsets from HCMV seronegative and seropositive donors. In contrast, adaptive NK cell subsets exhibited increased mitochondrial membrane potential (FIG. 2B). This increase was also evident when we sorted canonical and adaptive NK cells and analyzed mitochondria by confocal microscopy (FIG. 2C). We confirmed increased mitochondrial levels in adaptive NK cells by quantification of the ratio of mitochondrial DNA to nuclear DNA (mtDNA/nDNA) by quantitative RT-PCR. We observed an 81% increase in the mitochondrial DNA ratio in adaptive NK cells (FIG. 2D). Of note, no relative increase in the levels of reactive oxygen species (ROS), as determined by CellRox staining, was observed in adaptive NK cells (FIG. 2E).

To gain a deeper understanding with respect to the observed increases in OXPHOS and mitochondrial membrane potential in adaptive NK cells, we sorted canonical and adaptive NK cell subsets from the peripheral blood of five HCMV seropositive donors and performed RNA-seq analyses. Intriguingly, we observed a consistent pattern of increased expression of genes encoding components of the mitochondrial ATP synthase complex and electron transport chain (ETC) complexes I, III, IV in adaptive NK cell subsets (FIG. 2F). Among the most differentially expressed genes in this subset were NDUFS4, NDUFS5 and NDUFS5 (encoding components of ETC complex I) and UQCRH and UQCRB (encoding components of ETC complex III). We validated differential expression of these genes by sorting peripheral blood canonical and adaptive NK cells from HCMV seropositive donors and performing quantitative RT-PCR. We observed a statistically significant increase in the expression of each of these genes in adaptive NK cells relative to canonical NK cells (FIG. 2G). Gene Set Enrichment Analysis (GSEA) of the RNA-seq data also showed a statistically significant enrichment of genes involved in lipid catabolism in adaptive NK cells, consistent with previous reports (Liu et al., 2017), and a trend towards enrichment of genes involved in mitochondrial biogenesis and fatty acid metabolism (FIG. 13). Together, these data establish a unique metabolic profile characteristic of adaptive NK cells.

Figures 3A, 3B, 3C, 3D, 3E:
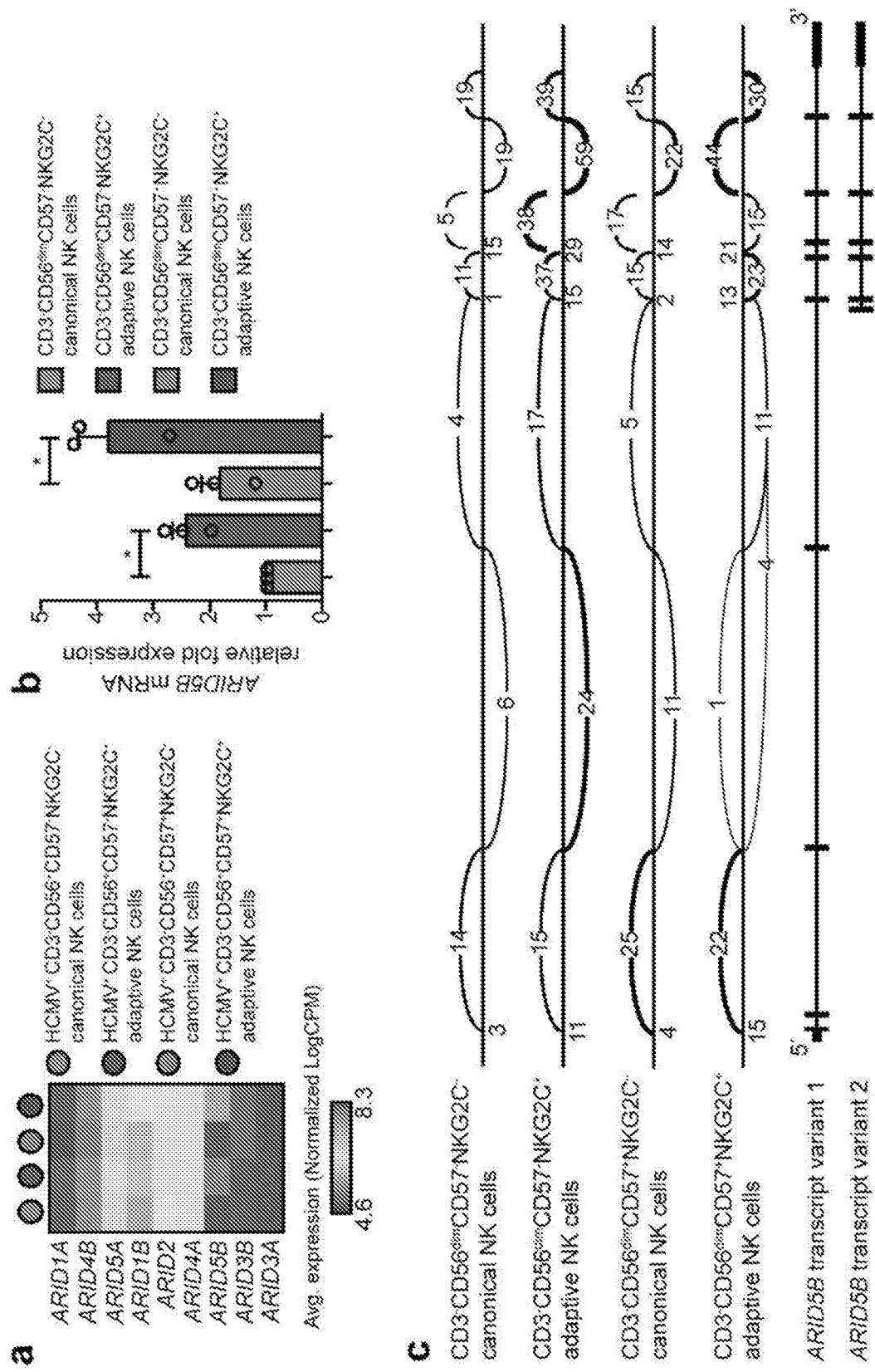
FIGS. 3A-3E demonstrate that ARID5B expression is elevated in adaptive NK cells. (A) Shown is a heat map of average normalized expression of genes belonging to the ARID family from the RNA-seq dataset. (B) Cumulative qRT-PCR data of ARID5B mRNA expression in the indicated canonical and adaptive NK cell subsets sorted from three HCMV-seropositive donors. All expression values were normalized against ACTB, and fold-expression values were determined for each subset relative to CD3$^-$CD56$^{dim}$CD57$^-$NKG2C$^-$ canonical NK cells. Results are from two independent experiments. (C) Sashimi plots of RNA-seq data from a representative donor showing genomic alignments of RNA-seq reads and splice junctions within the ARID5B locus. (D) Canonical and adaptive NK cells were sorted from two seropositive donors in two independent experiments. Western blots were performed with antibodies against ARID5B and β-actin. Shown is a representative blot from one donor (left panel) and quantification by densitometry for both donors (right panel). (E) Methylation patterns throughout the ARID5B locus generated from whole-genome methylation profiling of the indicated canonical and adaptive NK cell populations sorted from four HCMV-seropositive donors. Error bars represent S.E.M. Paired Student's t tests were used to determine statistical significance, *$p<0.05$.
Figure 10:
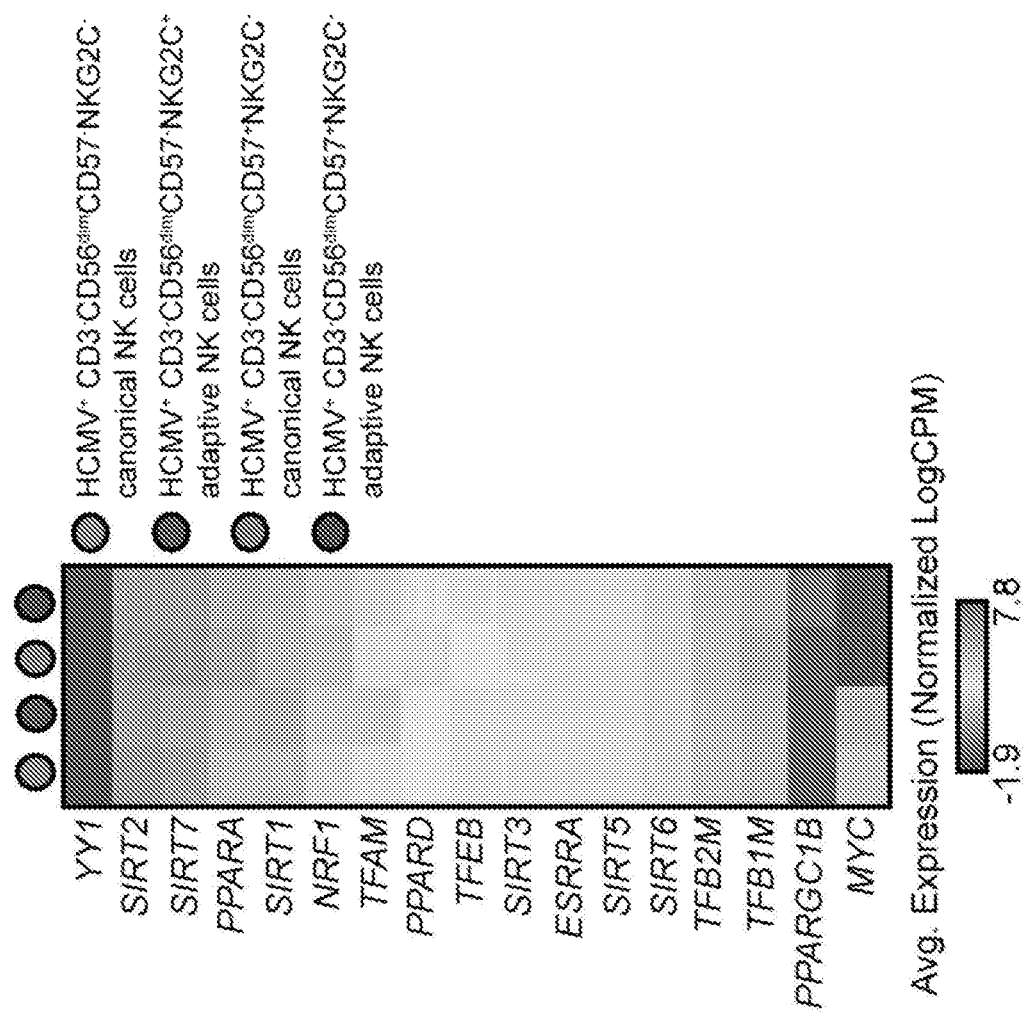
FIG. 10 demonstrates no difference in expression of multiple genes associated with mitochondrial biogenesis. The indicated subsets of canonical and adaptive NK cells were sorted from PBMCs isolated from five HCMV-seropositive donors in two independent experiments and used for RNA-seq analysis. Shown is a heat map of normalized log CPM expression values for genes with known associations in the promotion of mitochondrial biogenesis.

Expression of the Chromatin-Modifying Protein ARID5B is Induced in Adaptive NK Cells Several transcription factors and chromatin-modifying proteins have been implicated in mitochondrial biogenesis and cellular oxidative metabolism including members of the nuclear receptor superfamily, the peroxisome proliferator-activated receptors (PPARs) (Puigserver et al., 1998), and the estrogen-related receptors (Huss et al., 2004). In our RNA-seq analysis of gene expression from freshly isolated NK cells, we observed similar expression levels of PPAR and ERR family members when comparing canonical and adaptive NK cell subsets. We also observed similar expression levels of other genes encoding known transcriptional regulators of mitochondrial biogenesis and OXPHOS including YY1, MYC, TFAM, TFB2M, and TFB1M (Larsson et al., 1998; Falkenberg et al., 2002; Li et al., 2005; Cunningham et al., 2007) (FIG. 10). However, our analysis revealed higher expression of ARID5B specifically in adaptive vs. canonical NK cells (1.7-fold, adjusted p=0.013) (FIG. 3A). ARID5B belongs to a family of proteins that share a unique DNA-binding domain designated AT-rich interactive domain (ARID) (Kortschak et al., 2000). Knockout mice are viable at reduced frequencies, exhibit markedly stunted growth and are abnormally lean (Lahoud et al., 2001; Whitson et al., 2003). Although the immune system has not been studied in depth in these mice, abnormalities in B cell and T cell development, including significant decreases in bone marrow and thymic cellularities, have been reported (Falkenberg et al., 2002). Because ARID5B has previously been implicated in the direct regulation of metabolism in hepatocytes (Baba et al., 2011), direct regulation of inflammatory and lipid metabolism pathways in human CD14⁺ blood monocytes (Liu et al., 2017), and indirectly in the regulation of adipose cell metabolism through control of the FTO locus (Claussnitzer et al., 2015), we hypothesized that ARID5B also plays a role in regulating NK cell metabolism.

Increased expression of ARID5B in adaptive NK cells was confirmed by qRT-PCR using sorted subsets of canonical and adaptive NK cells from HCMV-seropositive donors (FIG. 3B). Two ARID5B isoforms have previously been identified: transcript variant 1 consists of 10 exons spanning 149,402 bp on chromosome 10, and transcript variant 2 has a unique first exon located within intron 4 of transcript variant 1 and shares the final six exons. To quantitatively visualize splice junctions and the relative expression of each isoform in canonical and adaptive NK cells, we used the Mixture of Isoforms package within the Integrative Genomics Viewer software to create Sashimi plots of our RNAseq alignment data. We found that ARID5B transcript variant 2 was enriched in adaptive NK cells (FIG. 3C). To confirm ARID5B variant expression at the protein level, we sorted canonical NK cells and adaptive NK cells from HCMV-seropositive donors and performed Western blots for ARID5B. Interestingly, ARID5B variant 2 was more abundant than variant 1 in both canonical and adaptive NK cells. The expression of both variants was higher in adaptive NK cells, with variant 2 being most abundant (FIG. 3D).

To determine whether there was a unique epigenetic signature in adaptive NK cells associated with the pattern of ARID5B expression, we examined data from our genome-wide DNA methylation arrays previously performed with sorted subsets of canonical and adaptive NK cells (Schlums et al., 2015). While the 5' region and transcriptional start site (TSS) upstream of ARID5B transcript variant 1 were hypomethylated to a similar extent in canonical and adaptive NK cells, we observed selective hypomethylation of the 5' region and TSS upstream of ARID5B transcript variant 2 in adaptive NK cells (P=2.32×10-12; FIG. 3E). Together, our data show a specific induction of ARID5B in adaptive NK cells with an enrichment of variant 2.

Figures 4A, 4B, 4C, 4D, 4E, 4F, 4G, 4H:
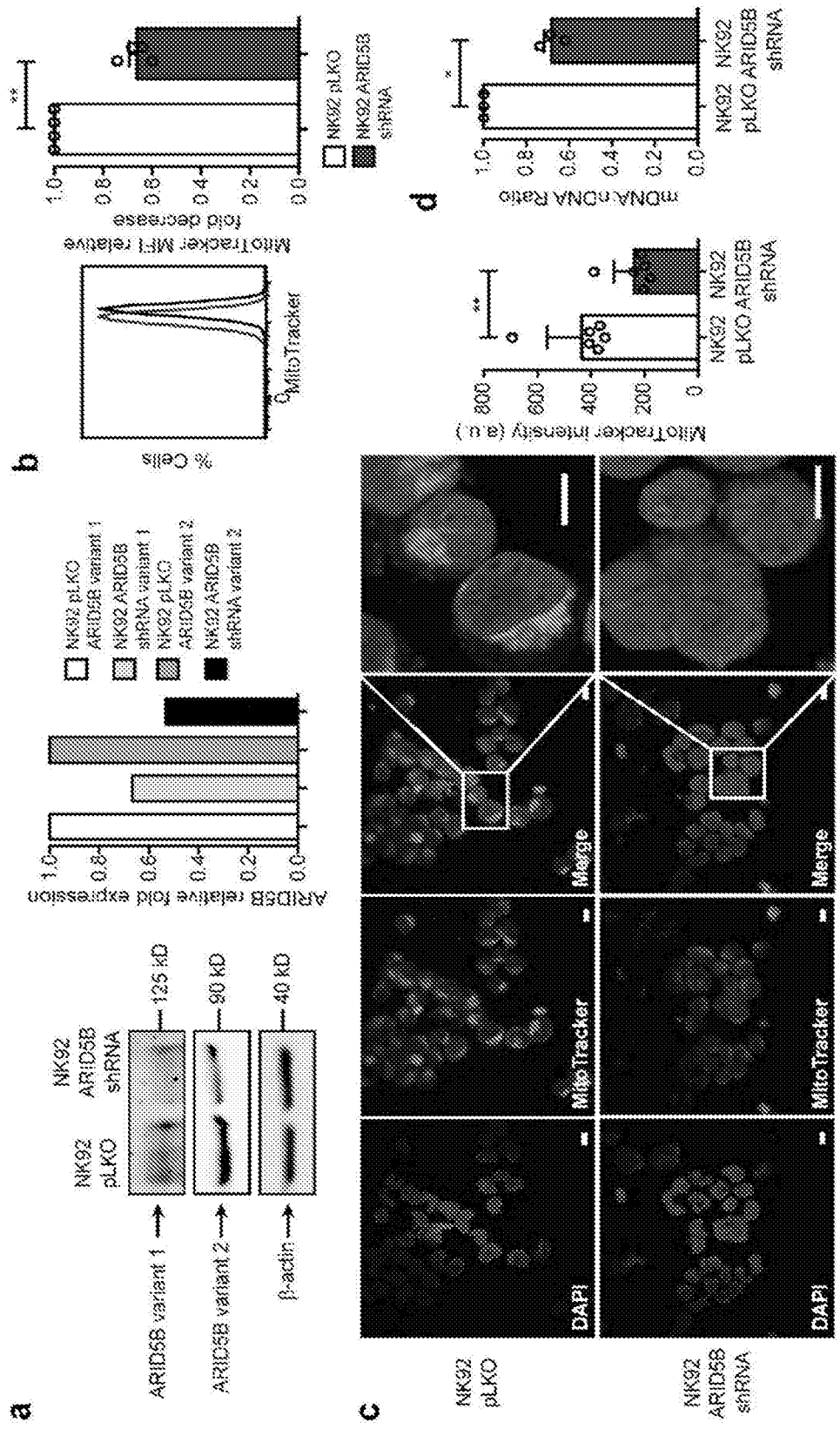
FIGS. 4A-4H demonstrate that knockdown of ARID5B leads to a decrease in mitochondrial membrane potential, oxidative mitochondrial metabolism, and IFN-γ production. NK-92 cells were transduced with an empty control pLKO vector or a pLKO vector containing an ARID5B-specific shRNA. (A) Western blot of ARID5B and β-actin in the control and shARID5B NK-92 lines (left panel) and quantification by densitometry (right panel). (B) Representative FACS plots (left panel) and cumulative fold differences in MitoTracker MFI values (right panel) from each indicated NK-92 cell line. Experiments were replicated 2 times. (C) The indicated NK-92 cell lines were stained with DAPI and MitoTracker dyes and visualized by confocal microscopy. Shown are representative images (left panel) and cumulative MitoTracker intensity values calculated from 11 individual cells (right panel). Results are from 2 independent replicates, with similar results observed in both experiments. (D) qRT-PCR was used to determine the ratio of mitochondrial DNA to genomic DNA for each indicated NK-92 cell line. Results are from 3 independent replicates. (E) OCR profiles of the control and shARID5B NK-92 cell lines in a representative experiment and averages for maximal respiration, ATP-linked respiration and spare respiratory capacity are shown. (F) ECAR profiles for the indicated NK-92 cell lines in a representative experiment and averages for maximal glycolysis and glycolytic reserve are shown. All cumulative OCR and ECAR results were replicated twice. (G) Quantification of ATP levels by bioluminescence in control and shARID5B cell lines. (H) Control and shARID5B NK-92 cells were cultured overnight with and without IL-12 and IL-18 prior to FACS analysis of NK cell functional readouts. Representative FACS plots and cumulative data of the frequencies of IFN-γ expression by NK-92 cells are shown. For G and H, experiments were replicated twice. Error bars represent S.E.M. Paired Student's t tests were used to determine statistical significance, $*p<0.05$, $**p<0.01$. n.s., not significant.
Figures 11A, 11B:
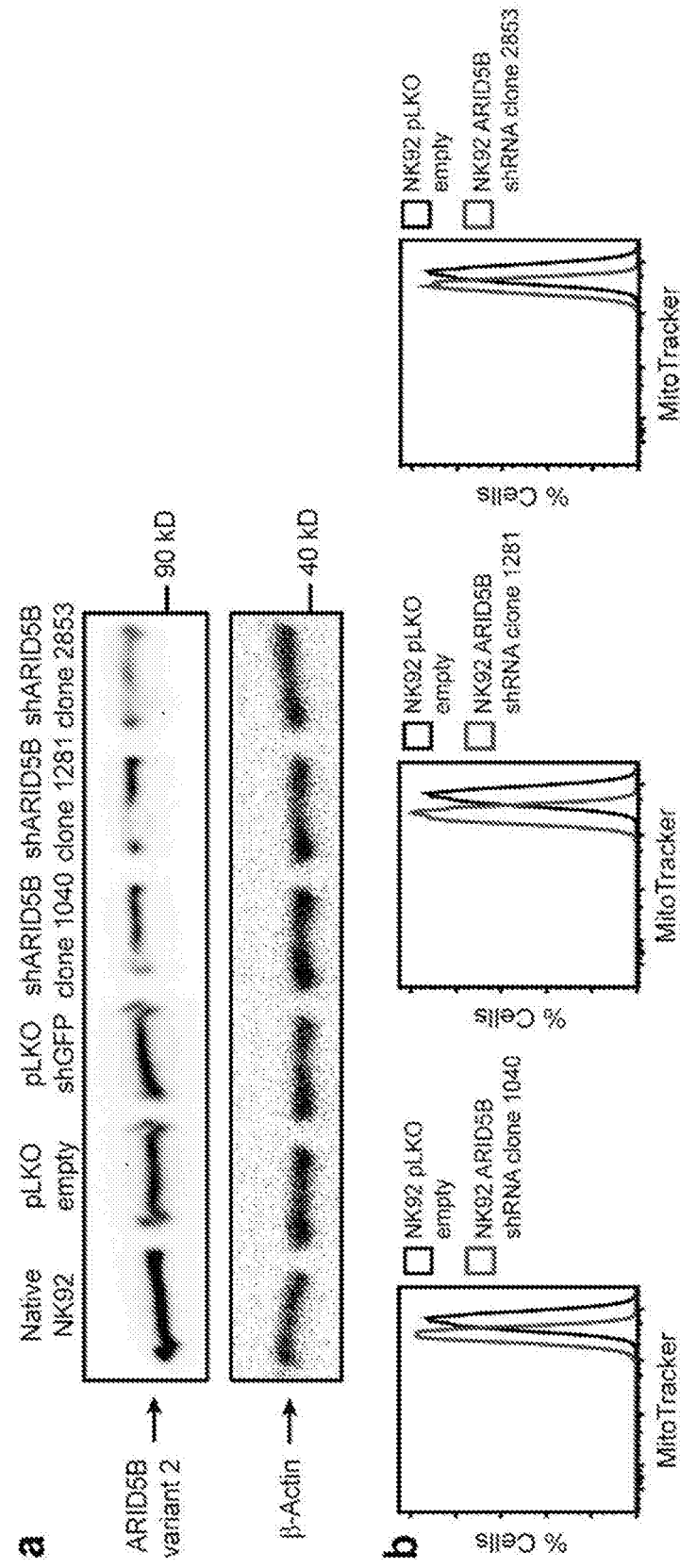
FIG. 11 demonstrates validation of ARID5B knockdown and decreased mitochondrial potential in NK-92 cells with three shARID5B clones. Two control vectors (pLKO empty and shGFP) along with 3 different shRNAs targeting ARID5B were transduced into NK-92 cells via lentiviral transduction. Stable NK-92 cell lines expressing each vector were generated by puromycin selection. (A) Western blots of ARID5B variant 2 in each line along with β-actin. (B) Histogram plots from FACS analysis of MitoTracker staining intensity in each shARID5B NK-92 cell line compared to the pLKO empty control.

ARID5B Modulation Impacts Mitochondrial Membrane Potential, Mitochondrial Oxidative Metabolism, IFN-γ Production and Survival in NK-92 Cells To test the hypothesis that ARID5B promotes NK cell metabolism, we knocked down ARID5B expression in the NK-92 NK cell line via lentiviral transduction. By this method, we were able to achieve a 40% reduction in ARID5B expression (FIG. 4A). Mitochondrial membrane potential, as quantified by MitoTracker, was reduced by 38% in ARID5B knockdown NK-92 cells (FIG. 4B), and similar results were observed when cells were visualized by confocal microscopy (FIG. 4C). Decreased mitochondrial membrane potential was observed in NK-92 cells transduced with three different shRNAs targeting ARID5B (FIGS. 11A-11B). To further confirm that ARID5B knockdown affected mitochondrial levels, we quantified the ratio of mitochondrial DNA to nuclear DNA by qRT-PCR and found that this ratio was reduced by 31% in ARID5B knockdown cells (FIG. 4D).

Next, we sought to determine whether knockdown of ARID5B had an effect on metabolism. Significant reductions in maximal respiration, ATP-linked respiration, and SRC were observed for ARID5B knockdown cells (FIG. 4E). In contrast, no overall differences were seen in glycolysis as determined by the ECAR profile of ARID5B knockdown cells, and both maximal glycolysis and glycolytic reserve were similar between ARID5B knockdown cells and controls (FIG. 4F). ATP levels were also similar between ARID5B knockdown cells and controls (FIG. 4G). Elevated mitochondrial mass, OXP HOS, and SRC are associated with superior T cell effector function (van der Windt et al., 2012, 2013; Buck et al., 2016). To determine whether ARID5B knockdown impacted NK cell function, we stimulated control and ARID5B knockdown NK-92 cells overnight with the inflammatory cytokines IL-12 and IL-18 to induce IFN-γ production. We observed a marked impairment of IFN-γ production by ARID5B knockdown NK-92 cells (FIG. 4H). Of note, no differences in degranulation or TNF production were observed between control and ARID5B knockdown cells in K562 stimulation assays (not shown).

Figures 5A, 5B, 5C, 5D:
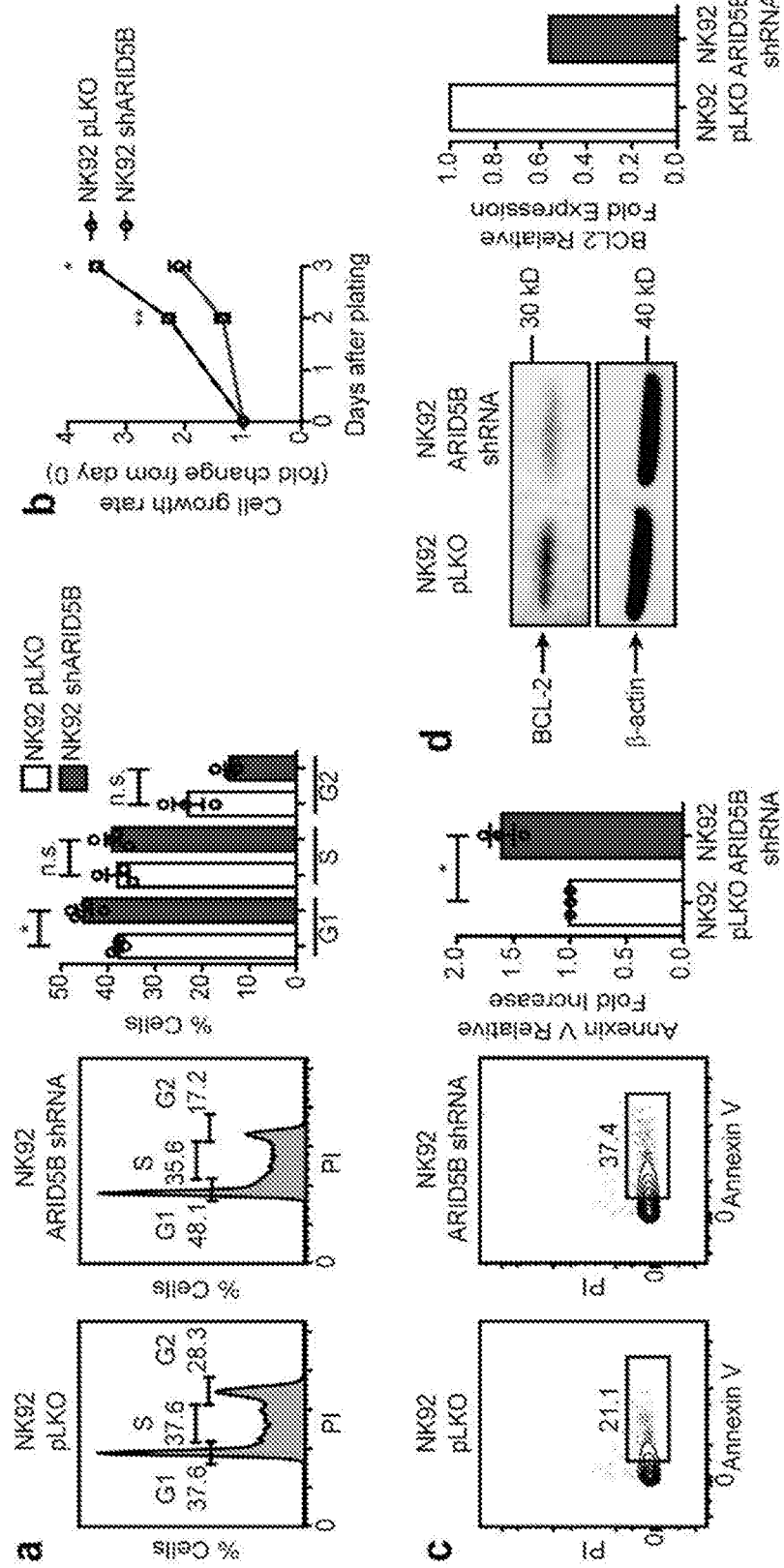
FIGS. 5A-5D demonstrate that knockdown of ARID5B leads reduced survival and expression of the pro-survival protein BCL-2. (A) Cell cycle analysis of control and shARID5B NK-92 cells by propidium iodide staining (PI). Shown are representative FACS plots for both NK-92 lines (left panel) and cumulative data of the percentages of cells in each cell cycle phase (right panel). Experiments were replicated twice. (B) Control and shARID5B NK-92 cells were plated at equal numbers, and viable cell counts were taken after 2 and 3 days in culture. Shown is cumulative fold expansion data for both lines. Results are from four replicates in two independent experiments. (C) Control and shARID5B NK-92 cells were stained with annexin V and propidium iodide and analyzed by flow cytometry. Shown are representative FACS plots gated on lymphocytes (left panel) and cumulative fold differences (right panel). (D) Western blot analysis of BCL-2 expression in control and shARID5B NK-92 cells. Shown is a representative blot (left panel) and fold decrease in shARID5B NK-92 cells calculated by densitometry (right panel). For C and D, experiments were replicated twice. Error bars represent S.E.M. Paired Student's t tests were used to determine statistical significance, $*p<0.05$, $**p<0.01$. n.s., not significant.

A role for ARID5B in supporting survival of T-ALL cell lines has been recently reported (Leong et al., 2017). We hypothesized that ARID5B may play a similar role in NK cells. To test this hypothesis, we performed cell cycle analyses using propidium iodide and found an accumulation of ARID5B knockdown cells in G1 relative to controls with a trend toward a decreased frequency of cells in G2 (FIG. 5A). Analysis of viable cell counts over 3 days in culture showed a significantly decreased growth rate for ARID5B knockdown cells (FIG. 5B). To determine whether the impaired growth of ARID5B knockdown cells could be due to decreased survival, we analyzed active apoptosis using annexin V. We observed a higher frequency of ARID5B knockdown cells undergoing apoptosis (FIG. 5C). As the inner mitochondrial membrane protein BCL-2 plays a key role in blocking programmed cell death (Sentman et al., 1991), and adaptive NK cells express elevated levels of BCL-2 (Zhang et al., 2013), we analyzed BCL-2 expression in control and ARID5B knockdown cells by Western blot. Interestingly, we observed a 44% reduction in BCL-2 expression in ARID5B knockdown cells (FIG. 5D).

Figures 6A, 6B, 6C, 6D, 6E, 6F, 6G:
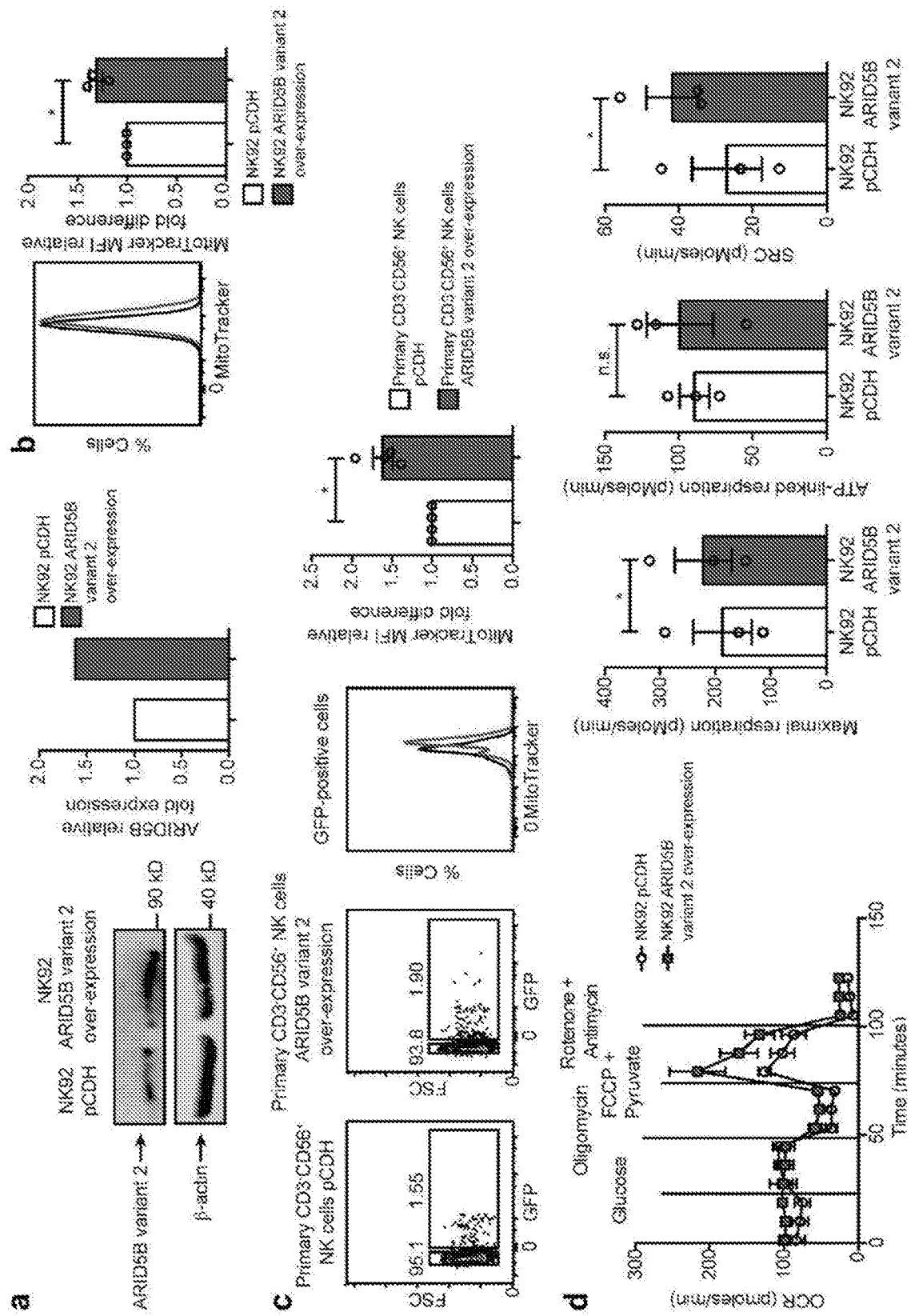
FIGS. 6A-6G demonstrate that over-expression of ARID5B results in increases in mitochondrial membrane potential, oxidative mitochondrial metabolism, and IFN-γ production. NK-92 cells were transduced with a control pCDH vector containing GFP or a pCDH vector containing GFP and ARID5B variant 2. (A) Western blot of ARID5B variant 2 and β-actin in each sorted GFP$^+$ NK-92 cell line (left panel) and image quantification by densitometry (right panel). (B) Mitochondrial membrane potentials were determined by MitoTracker staining and FACS analysis in sorted GFP$^+$ cells from the control and ARID5B variant 2 overexpression NK-92 lines. Cumulative data of the relative fold difference in MitoTracker staining between vectors is shown (right panel). Experiments were replicated twice. (C) Primary NK cells were transduced with the control or the ARID5B variant 2-overexpression vectors. Cells were analyzed for GFP expression and mitochondrial mass 72 hours post-transduction. Shown are representative FACS plots of GFP against forward scatter (FSC) in gated NK cells and MitoTracker histogram plots (left panels). Cumulative data from four donors of the relative fold difference in MitoTracker staining between vectors are also shown (right panel). Results are from two independent experiments. Similar results were observed in both experiments. (D) OCR profiles of the control and ARID5B variant 2-overexpressing NK-92 cell lines in a representative experiment and averages for maximal respiration, ATP-linked respiration, and spare respiratory capacity (SRC) are shown. (E) ECAR profiles for the indicated NK-92 cell lines in a representative experiment and averages for maximal glycolysis and glycolytic reserve are shown. OCR and ECAR experiments were replicated twice. (F) Quantification of ATP in control and ARID5B over-expressing cell lines in three independent replicates. (G) Control and ARID5B over-expressing NK-92 cells were cultured overnight with and without IL-12 and IL-18 prior to FACS analysis. Representative FACS plots and cumulative data of the frequencies of IFN-γ expression by NK-92 cells are shown. Experiments were replicated twice. Error bars represent S.E.M. Paired Student's t tests were used to determine statistical significance, $*p<0.05$, n.s., not significant.
Figures 6A, 6B, 6C, 6D, 6E, 6F, 6G:
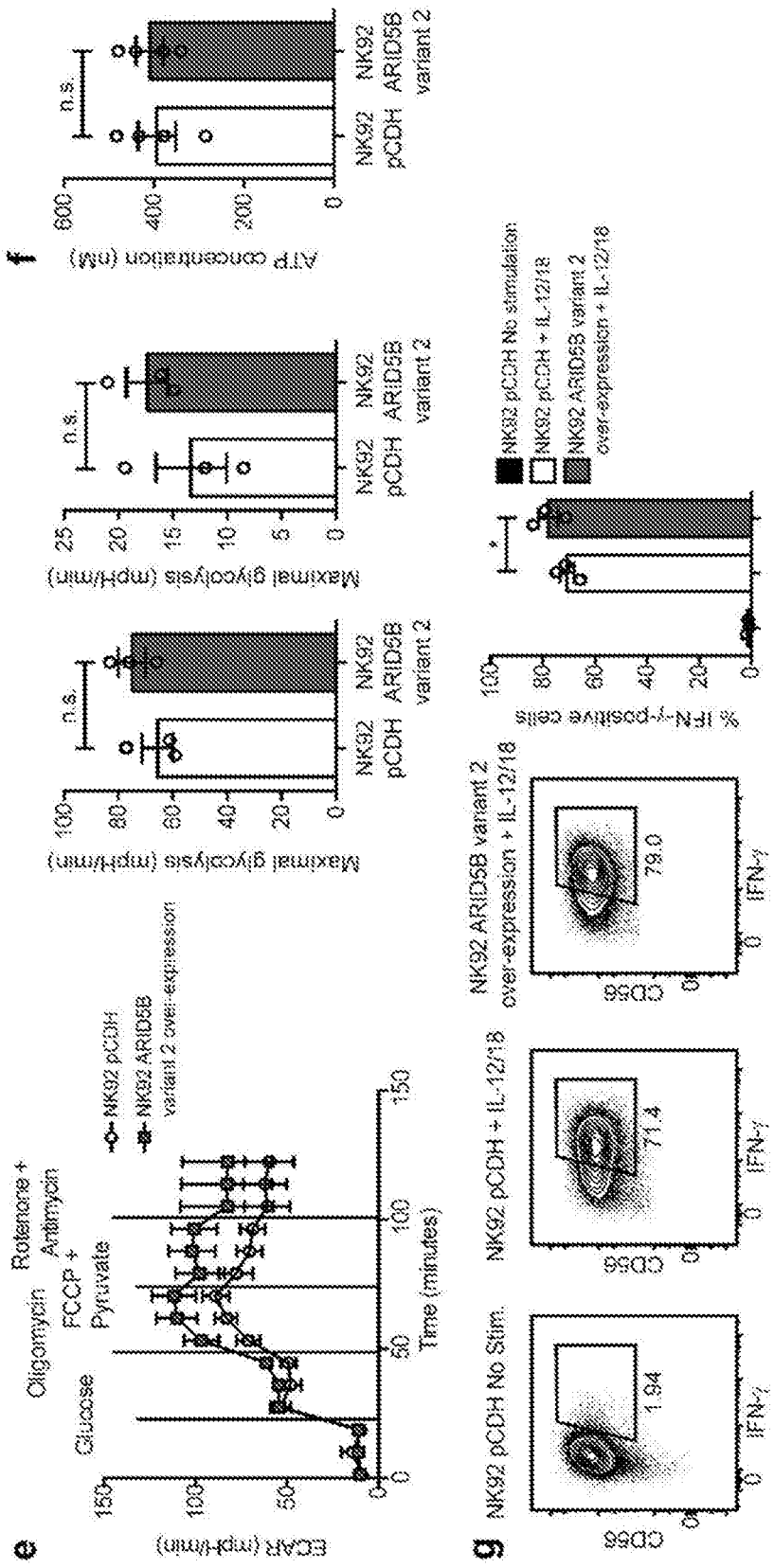

In addition to shRNA-mediated knockdown experiments, we also overexpressed ARID5B variant 2 in NK-92 cells via lentiviral transduction using the pCDH vector containing a GFP cassette the open reading frame for ARID5B variant 2. We observed a 1.62-fold increase in ARID5B in cells transduced with the overexpression vector relative to the empty vector control (FIG. 6A). ARID5B overexpression in NK-92 cells resulted in a 1.31-fold increase in mitochondrial membrane potential (FIG. 6B). Additionally, we transduced primary NK cells with the control and ARID5B overexpression vectors. We observed a 1.57-fold increase in mitochondrial membrane potential in cells overexpressing ARID5B (FIG. 6C). NK-92 cells overexpressing ARID5B exhibited higher maximal respiration and SRC, as determined by Seahorse analysis (FIG. 6D), but no statistically significant differences in glycolytic metabolism (FIG. 6E) or ATP levels (FIG. 6F) were observed. Functionally, ARID5B-overexpressing cells had higher frequencies of IFN-γ production in response to overnight IL-12 and IL-18 stimulation (FIG. 6G). Together, these data suggest that ARID5B influences mitochondrial membrane potential, oxidative mitochondrial metabolism, survival, and IFN-γ production.

Figures 7A, 7B, 7C, 7D, 7E, 7F, 7G:
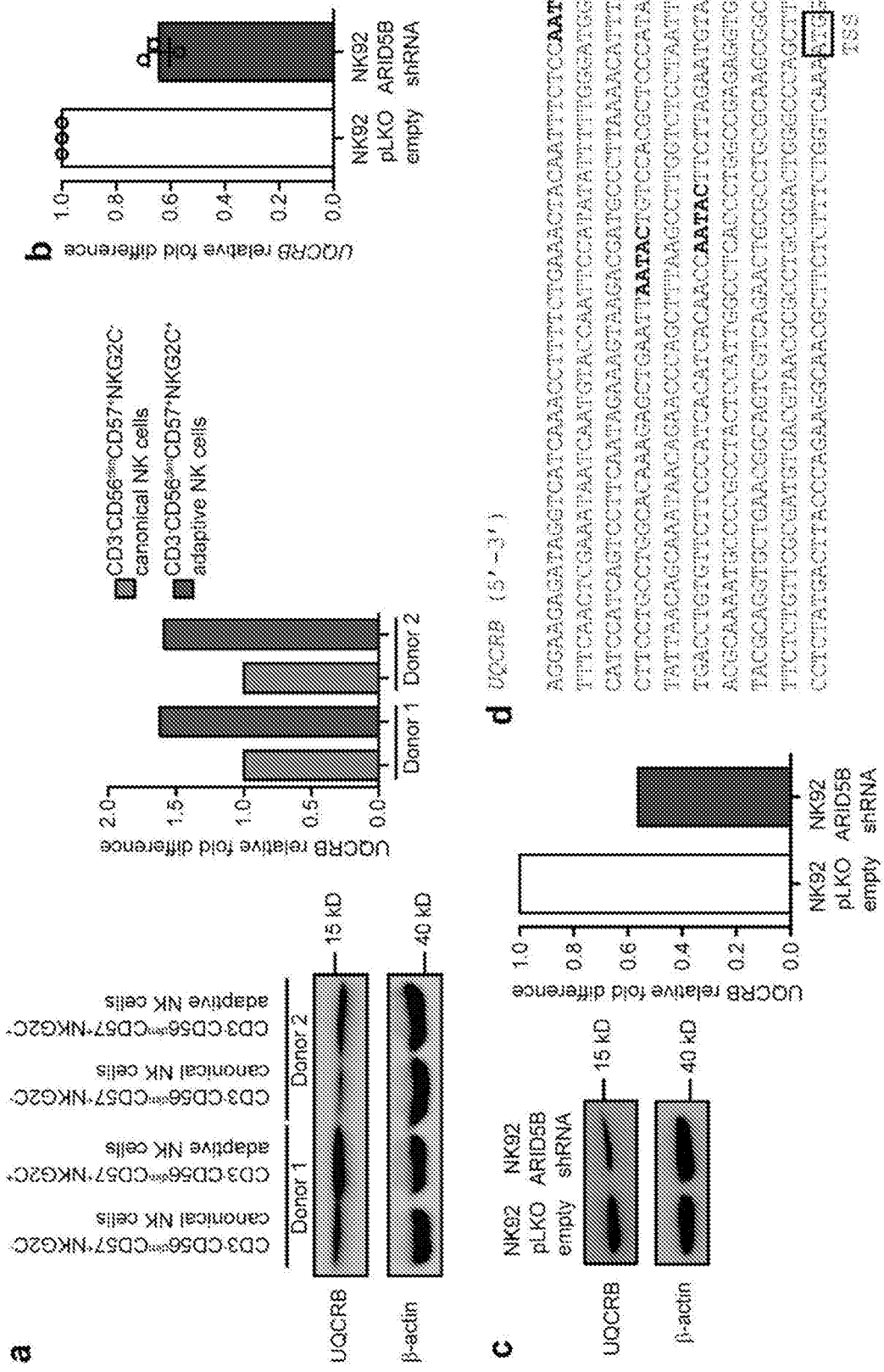
FIGS. 7A-7G demonstrate that ARID5B directly regulates UQCRB expression. (A) Canonical and adaptive NK cells were sorted from two HCMV-seropositive donors and used for Western blot analysis of UQCRB protein (left panel). Quantification by densitometry and determination of fold difference is also shown (right panel). (B) Determination of relative UQCRB mRNA expression in control versus shARID5B NK92 cells by qRT-PCR. Results are from three independent experiments. (C) Western blot of UQCRB protein expression in the control and ARID5B knockdown NK-92 lines (left panel) and relative UQCRB expression calculated by densitometry (right panel). (D) Shown is the sequence of the upstream proximal promoter region of UQCRB (SEQ ID NO:25) Putative core binding sites for ARID5B are highlighted in bold. The transcriptional start site (TSS) for UQCRB is also indicated. (E) Control and shARID5B NK-92 cells were used for ChIP assays to assess polymerase II and ARID5B binding to a control region far upstream of UQCRB (−1728 bp) and to the proximal UQCRB promoter (−351 bp). The ChIP assays were repeated five times in three independent experiments. Results are shown as the percentage of input. (F) Canonical and adaptive NK cells were sorted from the peripheral blood of three HCMV-seropositive donors. Sorted cells were used in ChIP assays to assess ARID5B binding to the control region far upstream of UQCRB (−1728 bp) and to the proximal UQCRB promoter (−351 bp). Results are from two independent experiments. (G) Canonical and adaptive NK cells were sorted from three HCMV-seropositive donors. ChIP assays were performed to assess H3K9Me2 levels in the control region far upstream of UQCRB and the within the proximal UQCRB promoter. Control isotype IgG antibody was included in all assays as a control for nonspecific binding. Results are from two independent experiments. Error bars represent S.E.M. Paired Student's t tests were used to determine statistical significance, $*p<0.05$, n.s., not significant.

ARID5B Directly Regulates Expression of the Electron Transport Chain Complex (ETC) III Component UQCRB, and UQCRB Knockdown Phenocopies the Metabolic and Functional Effects of ARID5B Knockdown Analysis of our RNA-seq data revealed a pattern of higher expression of several genes encoding components of the ETC in adaptive NK cell subsets (FIG. 2). We hypothesized that ARID5B could be directly or indirectly involved in the regulation of ETC genes. To test this hypothesis, we chose to study UQCRB in greater detail since it had the highest statistical significance for differential expression between canonical and adaptive NK cell among all ETC genes in our RNA-seq analysis (1.46 fold, adjusted p=0.037). UQCRB is a nucleus-encoded component of complex III in the mitochondrial respiratory chain, which plays an essential role in electron transfer for ATP production (Haut et al., 2003). To confirm elevated UQCRB expression in adaptive NK cells, we sorted canonical and adaptive NK cells from HCMV-seropositive donors and performed Western blots for UQCRB. In cells from both donors analyzed, UQCRB protein was strongly induced (1.97-fold) in adaptive NK cells (FIG. 7A). We also confirmed reduced expression of UQCRB in ARID5B knockdown NK-92 cells at the mRNA (FIG. 7B) and protein (FIG. 7C) levels.

Next, we searched the promoter region immediately upstream of the UQCRB TSS for potential ARID5B binding sites. ARID5B has been shown to preferentially bind an AATA(C/T) core consensus sequence (Whitson et al., 1999). Three such motifs were identified in the promoter of UQCRB (FIG. 7D). We then performed chromatin immunoprecipitation (ChIP) assays to analyze both polymerase II and ARID5B binding to the UQCRB promoter. A separate DNA sequence 1,728 bp upstream of the UQCRB TSS was included as a control for binding specificity in the assay. We found that both polymerase II and ARID5B bound to the UQCRB promoter in NK-92 cells, and binding was substantially diminished with ARID5B knockdown (FIG. 7E). To determine whether ARID5B was enriched within the UQCRB promoter in primary adaptive NK cells, we sorted canonical and adaptive NK cells and performed ChIP assays to analyze ARID5B binding to the control site upstream of UQCRB and to the UQCRB promoter. We observed ARID5B binding to the UQCRB promoter but not the upstream site in both canonical and adaptive NK cells and a significant enrichment of ARID5B binding in adaptive NK cells (FIG. 7F). ARID5B promotes gene expression through its interaction with plant homeodomain finger 2 (PHF2). The ARID5B-PHF2 complex is a specific histone demethylase complex that demethylates the inhibitory H3K9Me2 histone modification (Baba et al., 2011). To determine whether H3K9Me2 levels within the promoter of UQCRB were inversely correlated with ARID5B binding and UQCRB expression, we sorted primary canonical and adaptive NK cells and performed ChIP assays with an antibody specific for H3K9Me2. We observed significantly lower H3K9Me2 enrichment at the UQCRB promoter in adaptive NK cells (FIG. 7G).

Figures 8A, 8B, 8C, 8D, 8E, 8F:
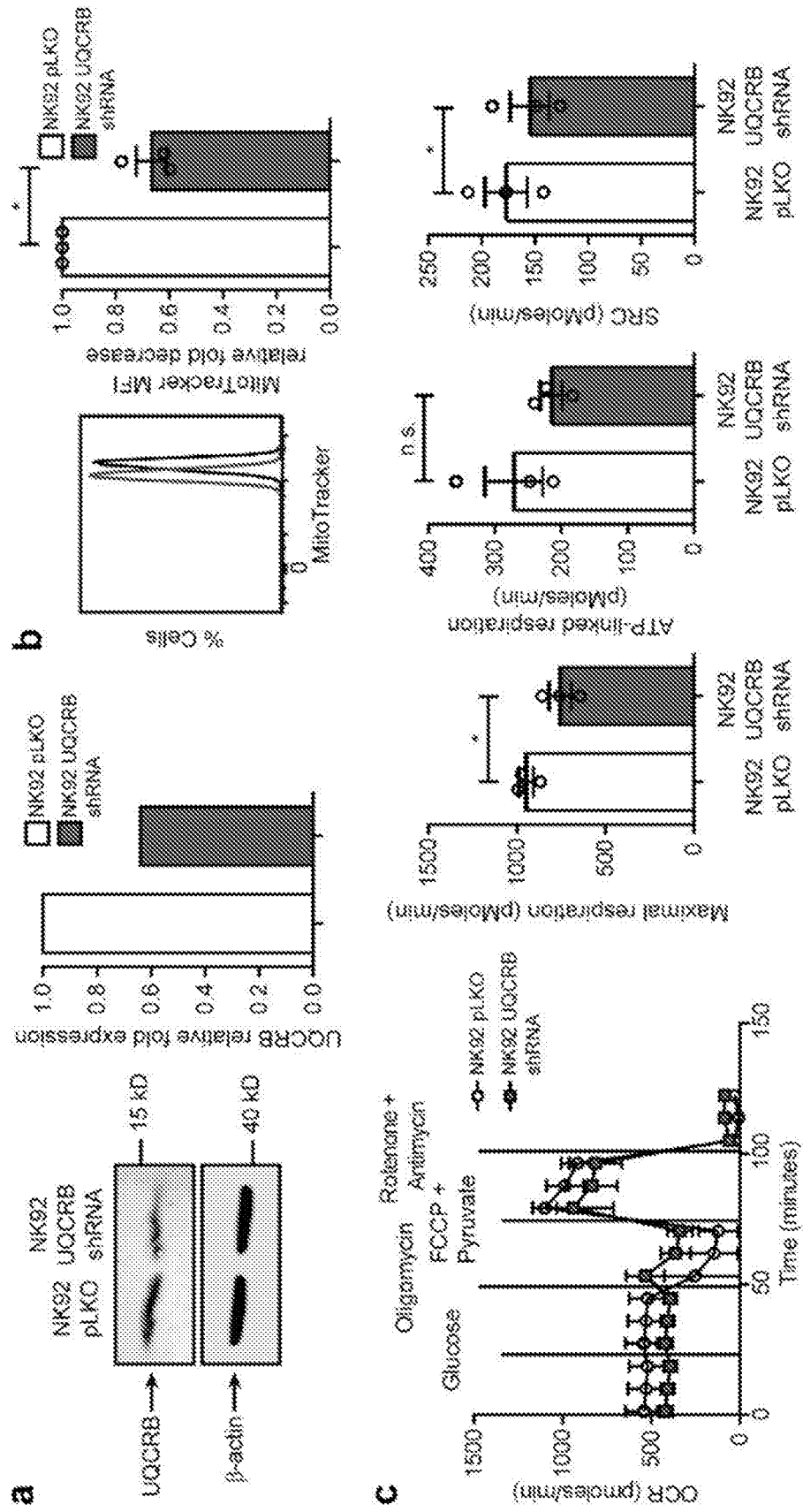
FIGS. 8A-8F demonstrate that knockdown of UQCRB leads to a decrease in mitochondrial membrane potential, oxidative mitochondrial metabolism, and IFN-γ production. NK-92 cells were transduced with an empty control pLKO.1 vector containing UQCRB-specific shRNA. (A) Western blot of UQCRB and β-actin protein expression in the control vector and shUQCRB NK-92 lines (left panel) and quantification by densitometry (right panel). (B) Representative FACS plots (left panel) and cumulative fold differences in MitoTracker MFI values (right panel) from each indicated NK-92 cell line. Experiments were replicated twice. (C) OCR profiles of the control and shARID5B NK-92 cell lines in a representative experiment and averages for maximal respiration, ATP-linked respiration and spare respiratory capacity (SRC) are shown. (D) ECAR profiles for the indicated NK-92 cell lines in a representative experiment and averages for maximal glycolysis and glycolytic reserve are shown. All cumulative OCR and ECAR results were replicated twice. (E) Quantification of ATP levels in control pLKO and shUQCRB cell lines. (F) Control and shUQCRB NK-92 cells were cultured overnight with and without IL-12 and IL-18 before FACS analysis of NK cell functional readouts. Shown are representative FACS plots and cumulative data of the frequencies of IFN-γ expression by NK-92 cells. (E and F) Experiments were replicated twice. Error bars represent S.E.M. Paired Student's t tests were used to determine statistical significance, $*p<0.05$. n.s., not significant.

Given the direct regulation of UQCRB expression by ARID5B, we next sought to determine the metabolic and functional effects of UQCRB knockdown. To this end, we knocked down UQCRB expression in NK-92 NK cells via lentiviral transduction. By this method, we were able to achieve a 37% reduction in UQCRB expression (FIG. 8A). Mitochondrial membrane potential was reduced by 33% in UQCRB knockdown NK-92 cells when analyzed by FACS (FIG. 8B). Significant reductions in maximal respiration and SRC were observed for UQCRB knockdown cells (FIG. 8C). In contrast, there was a trend toward increased glycolysis observed in UQCRB knockdown cells, though differences in maximal glycolysis and glycolytic reserve between UQCRB knockdown cells and controls were not statistically significant (FIG. 8D). ATP levels were similar between UQCRB knockdown cells and controls (FIG. 8E). Functionally, we observed a marked impairment of IFN-γ production by UQCRB knockdown NK-92 cells in response to IL-12 and IL-18 stimulation (FIG. 8F). Overall, these data show that ARID5B directly controls UQCRB expression, and knockdown of UQCRB phenocopies ARID5B knockdown.

Discussion

We propose a model in which increased metabolism supports adaptive NK cell expansion and survival. The enhanced metabolism observed in adaptive NK cells appears to be dependent, at least in part, on increased expression of ARID5B and its induction of genes encoding components of the ETC, including the ETC complex III gene UQCRB. ARID5B also appears to play a significant role in NK cell survival, as ARID5B knockdown is associated with increased apoptosis and reduced BCL-2 expression. Because BCL-2 localization to the mitochondria counteracts the production of ROS, a byproduct of ETC activity (Giménez-Cassina and Danial, 2015), elevated BCL-2 in adaptive NK cells may be important to limit oxidative stress. Whether ARID5B directly regulates BCL-2 and other survival genes requires further investigation.

One caveat to the knockdown and over-expression studies presented here is that they were performed using NK-92 cells due to the difficulty of transducing or transfecting primary NK cells at high enough frequencies to use in metabolic and functional analyses. NK-92 cells, like all transformed cells, have significant metabolic alterations that could be confounding. That being said, our model is consistent with previous work showing that CD8$^+$ T cells lacking MCJ/DnaJC15, a repressor of respiratory chain activity, exhibit increased OXPHOS, more mitochondrial mass, enhanced survival during cytokine withdrawal, an increased ability to secrete IFN-γ and superior control of viral infection (Champagne et al., 2016). The metabolic and functional effects of ARID5B on cytotoxic lymphocyte metabolism appear to be very similar to those reported for MJC/DnaJC15 loss. Our results are also consistent with recent work showing that ETC activity, but not ATP production, is essential for IFN-γ production in effector memory CD8+ T cells (Bantug et al., *Immunity.* 48:542-555.e6, 2018). We conclude that ARID5B can enhance aspects of NK cell metabolism and IFN-γ production by control of ETC gene expression.

Given our results showing increased expression of ARID5B in adaptive NK cells and a role for ARID5B in promoting OXPHOS and survival, it is possible that ARID5B plays a similar role in controlling metabolism and survival in T and B cell memory subsets. In support of this idea, transcript expression data from the Immunological Genome Project (see immgen.org on the World Wide Web) show an increase in ARID5B expression in throughout human B cell maturation with a marked increase in ARID5B expression in mature class-switched B cells relative to non-class-switched B cells. Similarly, both CD4$^+$ and CD8$^+$ central and effector memory T cells express significantly higher ARID5B transcript levels relative to naïve subsets. As such, induction of ARID5B may represent a general mechanism supporting cellular persistence and immunological memory formation.

Figures 12A, 12B:
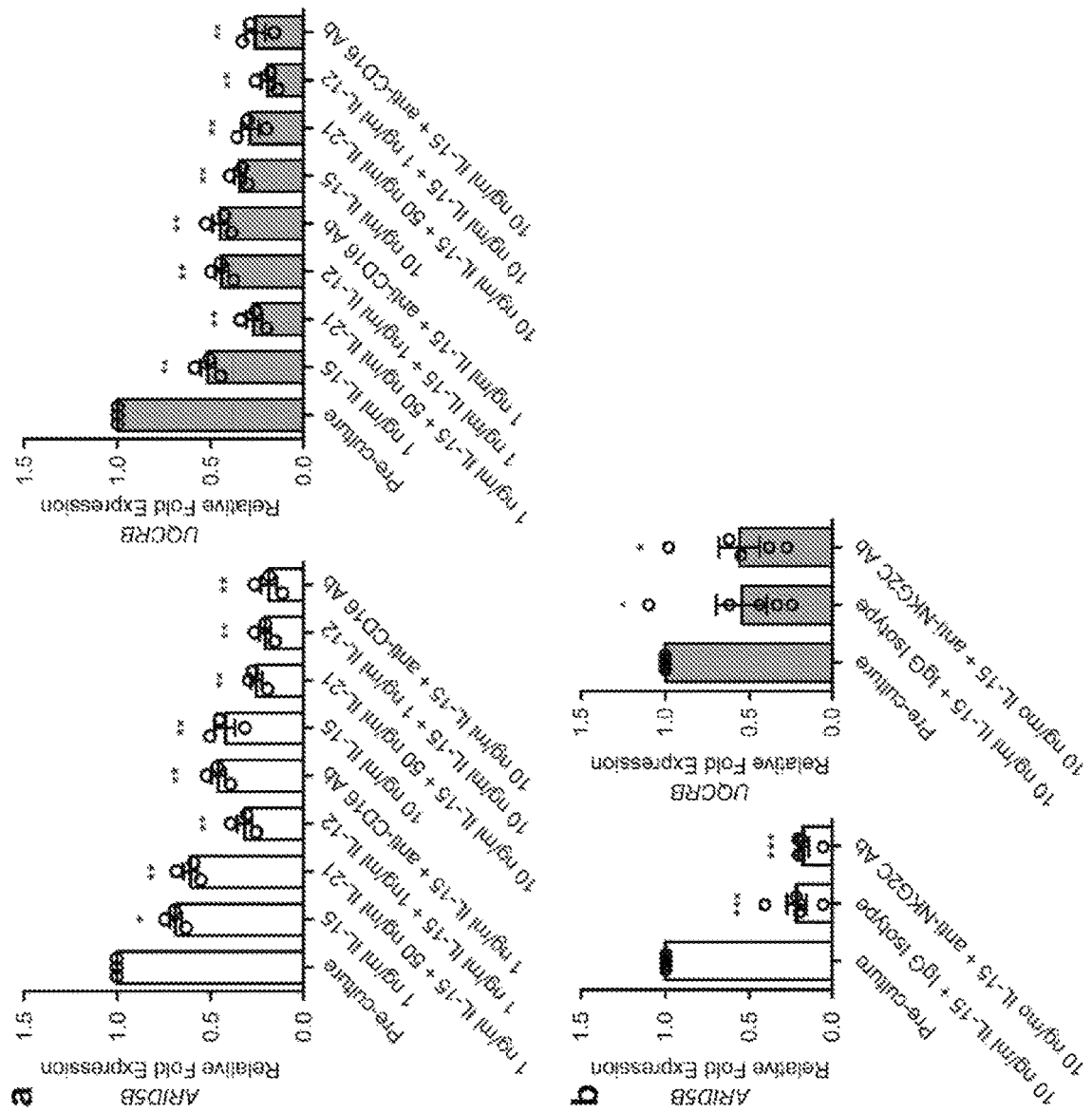
FIGS. 12A-12B demonstrate that ARID5B and UQCRB are not induced by inflammatory cytokines or signaling through activating receptors. (a) $CD3^-CD56^+$ NK cells were isolated from peripheral blood of three donors. A fraction of cells was lysed immediately, and RNA was harvested for quantitative RT-PCR (qRT-PCR). The rest of the cells were cultured with either 1 ng/ml or 10 ng/ml IL-15±50 ng/ml IL-21, 10 ng/ml IL-12 or an anti-CD16 antibody. All reagents were added at the beginning of culture with the exception of IL-12, which was added only during the last 16 hours. Cells were harvested after 72 hours, and RNA was harvested for qRT-PCR. Shown is cumulative data of ARID5B and UQCRB transcript fold expression in each culture condition relative to pre-culture. All values are normalized to ACTB. Results are from 1 experiment. (b) $CD3^-CD56^+$ NK cells were isolated from peripheral blood of five HCMV-seropositive donors. A fraction of cells was lysed immediately, and RNA was harvested for qRT-PCR. The rest of the cells were cultured with 10 ng/ml IL-15 and either an IgG isotype antibody or an anti-NKG2C agonist antibody. Cells were harvested after 72 hours, and RNA was harvested for qRT-PCR. Shown is cumulative data of ARID5B and UQCRB transcript fold expression in each culture condition relative to pre-culture. All values are normalized to ACTB. Results are from two independent experiments. Statistical significance was determined by comparing each culture condition to the pre-culture controls. Error bars represent S.E.M. Paired t-tests were used to determine statistical significance, $*p<0.05$, $p<0.01$, $*p<0.001$.

How ARID5B expression is induced in adaptive NK cells is unclear. We performed experiments where NK cells were cultured with inflammatory cytokines (IL-15, IL-21, IL-12) and CD16 or NKG2C agonist antibodies but did not observe an induction of ARID5B. In fact, ARID5B transcript expression levels decreased in during activation in vitro (FIG. 12). In transformed T cells, ARID5B is a downstream target of the oncogenic transcription factor T cell acute lymphocytic leukemia 1 (TAL1) and is required for the survival and growth of acute lymphoblastic leukemia T cells (Leong et al, *Genes Dev.* 31:2343-2360). Whether TAL1 can induce ARID5B expression in primary lymphocytes has yet to be determined.

Together, our results support the notion that adaptive NK cells that arise in response to HCMV infection have defined characteristics of immunological memory. Hallmarks of T cell memory, including increases in OXP HOS, SRC, and mitochondrial mass, are also evident in adaptive NK cells from HCMV-seropositive individuals. We identify ARID5B as a transcription factor that may promote the long-term persistence of adaptive NK cells after HCMV reactivation in HCT recipients and their enhanced ability to produce IFN-γ. Moreover, our results suggest that ARID5B may represent a common factor important to support recall responses to secondary infections. Strategies to increase ARID5B and therefore enhance mitochondrial function and NK cell persistence may be of therapeutic value in NK cell immunotherapy.

Materials and Methods

Cell source: Typed HCMV-seropositive and HCMV-seronegative blood products drawn from healthy, consenting donors were purchased from Memorial Blood Bank (Minneapolis, MN). All samples were de-identified before receipt, and the institutional review board at the University of Minnesota approved these studies. All research was conducted in accordance with the Declaration of Helsinki. All blood samples were drawn with donor consent.

Primary cell isolation, cell lines and culture: PBMCs were isolated by density gradient centrifugation using Ficoll-Paque Premium (GE Healthcare). For sorting experiments, T cells and B cells were depleted using anti-CD3 and anti-CD19 magnetic beads (STEMCELL Technologies). For phenotypic analyses, NK cells were isolated by negative selection using the EasySep Human NK Cell Isolation Kit (STEMCELL Technologies). Primary cells were cultured overnight in RPMI media (Gibco) supplemented with 10% fetal bovine serum (FBS) in the absence of cytokines. NK-92 and K562 cells were obtained from ATCC and cultured according to their instructions. The following cytokines were used in culture experiments: IL-15 (NCI), IL-21 (eBiosciences) and IL-12 (R&D Systems). Plate-bound anti-NKG2C agonist antibody (gift from J. P. Houchins at R&D Systems) was used in some culture experiments.

Flow cytometry and cell sorting: For flow cytometry, fluorochrome-conjugated antibodies to the surface epitopes CD3 (OKT4, Biolegend), CD56 (HDCD56, Biolegend), CD57 (NK-1, BD Biosciences), NKG2C (134591, R&D Systems), CD107a (H4A3, BD Biosciences), were used. Intracellular EAT-2 was stained using a rabbit polyclonal antibody (Proteintech Group) followed by secondary staining with fluorochrome-conjugated anti-rabbit reagents (Invitrogen). Intracellular staining of cytokines was performed using fluorochrome-conjugated antibodies against IFN-γ (B27, BD Biosciences) and TNF (MAb11, Biolegend). For phenotypic analyses, PBMCs or purified NK cells were surface stained with the indicated antibodies along with a fixable dead cell stain (Invitrogen) in FACS buffer (PBS supplemented with 2% FBS and 2 mM EDTA) and fixed in 2% formaldehyde. For intracellular staining, cells were permeabilized in 0.05% Triton X-100 (Sigma). Flow cytometry data was acquired on a LSR II instrument (BD Biosciences) and analyzed with FlowJo (v10, Tree Star). MitoTracker Deep Red, CellRox (ThermoFisher) and propidium iodide (Sigma) staining was performed according the manufacturer's instructions. For sorting experiments, PBMCs were stained with the indicated antibodies and sorted to >95% purity on a FACS Aria II instrument (BD Biosciences).

Seahorse metabolism, ATP quantification, glucose uptake and annexin V assays: Seahorse assays were performed according the manufacturer's instructions with modifications to simultaneously analyze glycolysis and oxidative mitochondrial metabolism using the Seahorse XF Glycolysis Stress Test Kit and the Seahorse XF Cell Mito Stress Test Kit (Agilent Technologies). Briefly, NK cells were washed and resuspended in glucose-free media (Gibco). $1 \times 10^6$ cells per well were spun down onto plates coated with poly-L-lysine. Triplicate wells were set up for experiments using $CD3^-CD56^+$ NK cells isolated from bulk PBMCs and transduced NK-92 cells. Glucose, oligomycin, phenylhydrazone (FCCP), sodium pyruvate, rotenone, and antimycin A were serially injected to measure metabolic function. Plates were analyzed using an $XF^e$ 24 Extracellular Flux Analyzer (Agilent Technologies). For experiments using sorted primary NK cells, $5 \times 10^5$ cells from each population were plated in triplicate wells and analyzed using the same protocol above using an $XF^e$ 96 Extracellular Flux Analyzer (Agilent Technologies). SRC measurements were calculated as average maximal OCR values minus average basal OCR values. ATP levels were calculated as average basal OCR values minus average post-oligomycin OCR values. Glycolysis was calculated as average post-glucose ECAR values minus average basal ECAR values. Glycolytic reserve was calculated as average maximal ECAR values minus post-glucose ECAR values. For glucose uptake assays, NK cells were cultured with 10 ng/ml IL-15 alone ±anti-CD16 antibody (1 µg; 3G8; BD Biosciences) for 1 hour or ±PMA (25 ng/ml) and ionomycin (1 µM) (Sigma) for 15 minutes in media containing the fluorescently labeled glucose analog 2-(N-(7-Nitrobenz-2-oxa-1,3-diazol-4-yl)Amino)-2-Deoxyglucose (2-NBDG; Life Technologies) at a final concentration of 50 µM. For ATP quantification assays, $1 \times 10^2$ NK cells per well were assayed using the ATP Bioluminescence Assay Kit HS II (Sigma) and analyzed on an Infinite M200 PRO Luminometer (Tecan). For ATP assays using metabolic inhibitors, etomoxir (40 µM), 2DG (50 mM) and UK5099 (50 nM) (Sigma) were added 10 minutes prior to cell lysis and ATP determination. For cell apoptosis analysis, cells were stained with annexin V FITC and PI (ThermoFisher) according to the manufacturer's instructions.

Confocal microscopy: For mitochondria imaging experiments, cells were stained with MitoTracker Deep Red dye (ThermoFisher) according to the manufacturer's instructions. After staining, cells were washed 3 times with PBS and spun onto slides with a Cytospin 2 (Shandon). Cells were fixed and mounted in Vectashield with DAPI staining dye (Vector Labs). Images were acquired with an Olympus BX upright microscope equipped with a Fluoview 1000 confocal scan head with a 60× oil immersion objective (Olympus). Image processing and fluorescence intensity quantification was performed using Icy open platform software (see icy.bioimageanalysis.org on the World Wide Web).

RNA-seq experiments: NK cells from the peripheral blood of HCMV-seropositive donors were analyzed by FACS for surface expression of CD3, CD56, CD57, and NKG2C and intracellular expression of FcεRγ, EAT-2, and SYK. Five donors were selected based on high adaptive $CD56^{dim}CD57^+NKG2C+NK$ cell frequencies (≥15% of all $CD3^-CD56^{dim}NK$ cells) and lack of FcεRγ, EAT-2, and/or SYK specifically within the NKG2C$^+$ population. Canonical $CD3^-CD56^{dim}CD57^-NKG2C^-$ NK cells, canonical $CD3^-CD56^{dim}CD57^+$ NKG2C$^-$NK cells, adaptive $CD3^-CD56^{dim}CD57^-NKG2C^+$ NK cells, and adaptive $CD3^-CD56^{dim}CD57^+NKG2C^+$ NK cells were sorted. RNA was extracted using an RNeasy Plus Micro Kit (Qiagen). Barcoded TruSeq RNA v2 libraries (Illumina) were created, and libraries were sequenced on a HiSeq 2500 (Illumina) as paired end 100 bp. STAR version 2.4.0d was used to align the RNA-seq reads to the human genome reference build GRCh37 (hg19). The Ensembl gene annotation version 75 was provided as gene transfer format (gtf) for exon junction support. For each sample reads were assigned to genes and summarized using FeatureCounts (subread package version 1.4.5-p1). Raw read counts were read into R (version 3.2.0) and subjected to normalization by the trimmed mean of M-values normalization method implemented in the R/bioconductor edgeR package and variance normalized using voom from the R/bioconductor limma package. All genes with at least one count per million (CPM) mapped reads in at least two samples were analyzed further. Differential gene expression was performed using the R/bioconductor limma package. RNA-seq data can be found under the GEO accession no. GSE117614.

Genome-wide DNA methylation analyses: The indicated NK cell subsets were sorted from the peripheral blood of HCMV-seropositive donors, and DNA was extracted using the DNeasy Blood & Tissue Kit (Qiagen). The EpiTect Bisulfite Kit (Qiagen) was used to convert unmethylated cytosines to uracils. Bisulfite-converted DNA was analyzed with the Infinium Human Methylation450 BeadChip platform (Illumina). A comprehensive description of the analysis pipeline with linked raw data has been published previously (Schlums et al., 2015. *Immunity*. 42:443-456).

Plasmids and retroviral transduction: All ARID5B shRNA, UQCRB shRNA, and control vectors (pLKO.1) were purchased from Open Biosystems. The shRNA targeting sequences from the three ARID5B clones tested were: clone 1040; 5'-CCGGGCCTTCAAAGAGAACCATT-TACTCGAGTAAATGGTTCTCTTTGAAGGCTTT TTTG -3' (SEQ ID NO:1), clone 1281; 5'-CCGGCGA-TAGAACGAATACCCTATTCTCGAGAATAGGGTAT-TCGTTCTATCGTTT TTTG -3' (SEQ ID NO:2), and clone 2853; 5'-CCGGCGAGGAAGAAACGAACGT-GATCTCGAGATCACGTTCGTTTCTTCCTCGTTT TTTG -3' (SEQ ID NO:3). The shRNA targeting sequence from the UQCRB clone tested was 5'-CCGGCCTAAAGAGCAGTGGAC-CAAACTCGAGTTTGGTCCACTGCTCTTTAGGTTT TTG -3' (SEQ ID NO:4). ARID5B variant 2 overexpression vectors were created by cloning a custom gBlock gene fragment of the ARID5B variant 2 open reading frame (Integrated DNA Technologies) into the pCDH vector (Open Biosystems) by restriction digest using EcoR1 and BamH1 (New England Biolabs) and transfected along with lentiviral packaging vectors into 293T cells using 1 µg/µl polyethylenimine (Polysciences). The sequence for ARID5B variant 2 (GenBank accession number NM_032199) was from the GRCh37/hg19 genome assembly on the UCSC genome browser site (see genome.ucsc.edu on the World Wide Web). Supernatants containing viral particles were used to transduce NK-92 cells or primary NK cells via spin transduction. Stable NK-92 lines were selected with puromycin (Sigma).

For transduction experiments using primary NK cells, transduced cells were cultured for 48 hours in a low concentration (1 ng/ml) IL-15 before FACS analysis.

Western blot: Cells were lysed in ice-cold lysis buffer and run on 10% SDS-PAGE gels. Proteins were then transferred to nitrocellulose membranes and incubated at room temperature in 5% BSA in TTBS (50 mM Tris-HCl, 150 mM NaCl, and 0.05% Tween 20, pH 7.4) buffer for 1 hour. Membranes were then incubated overnight with primary antibodies against ACTB (sc-47778, Santa Cruz Biotechnology), ARID5B (NBP1-83622, Novus Biologicals), BCL-2 (ab692, Abcam) or UQCRB (ab190360, Abcam) at a dilution of 1:1000 in TTBS. Membranes were washed and incubated with anti-rabbit or anti-mouse horseradish peroxidase secondary antibodies at a 1:2000 dilution for 1 hour. Immunoreactive bands were imaged on a UVP Imaging System with ECL reagents (ThermoFisher). Densitometry analyses were performed using Image J software (National Institutes of Health).

Quantitative RT-PCR: For quantification of gene expression, cells were lysed in RLT buffer (Qiagen), and RNA was extracted using an RNeasy Plus Micro Kit (Qiagen). cDNA was synthesized from RNA using Superscript IV Reverse Transcriptase (ThermoFisher). qRT-PCR reactions were performed using SYBER Green PCR Master Mix (Applied Biosystems). qRT-PCR-based assays for determining the ratio of mitochondrial to nuclear DNA were performed as previously described. Primer sequences used for analysis of gene expression and DNA quantification are as follows:

ACTB fwd, 5'-CCC AGC ACA ATG AAG ATC AA-3' (SEQ ID NO:5); ACTB rev, 5'-ACA TCT GCT GGA AGG TGG AC-3' (SEQ ID NO:6); NDUFS4 fwd, 5'-GGA GCT ATG ACA TTG AAG AGA GG-3' (SEQ ID NO:7); NDUFS4 rev, 5'-TGC ACA GCT GAC TTT ATT CACA-3' (SEQ ID NO:8); NDUFS5 fwd, 5'-GCA GCG GGA TAA GCT GAT AA-3' (SEQ ID NO:9); NDUFS5 rev, 5'-CTT TGA CAA GGA GGT TTG TCG-3' (SEQ ID NO:10); NDUFB5 fwd, 5'-CTC CGA AAG CAA CTC CTG AC-3' (SEQ ID NO:11); NDUFB5 rev, 5'-ACT GGA AGC CAA ACT CCT CA-3' (SEQ ID NO:12); UQCRH fwd, 5'-CCA CAA ACT CTT TAA CAA CTT GAAA-3' (SEQ ID NO:13); UQCRH rev, 5'-CAA ATG GTA CAT CCA AAA CCA-3' (SEQ ID NO:14); UQCRB fwd, 5'-GAA AGA GAA GAA TGG GCA AAGA-3' (SEQ ID NO:15); UQCRB rev, 5'-GAA TTC AAA AAC TCC AGC CATT-3' (SEQ ID NO:16); UQCRB-351 bp ChIP fwd, 5'-CTT CCT GCC TGG CAC AAA GAG CTG AA-3' (SEQ ID NO:17); UQCRB-351 bp ChIP rev, 5'-GGG AAG AAC ACA GGT CAG GAA TTA GGA GAC CA-3' (SEQ ID NO:18); UQCRB-1,728 bp ChIP fwd, 5'-CCA GTA ACT ATC AGT CAT GCT AGC TCC CCC TAA TTG-3' (SEQ ID NO:19); UQCRB-1,728 bp ChIP rev, 5'-TCC ACC CAC GTC AGC CTC CCA AAA-3' (SEQ ID NO:20); mitochondrial transfer RNA-Leu (URR) fwd, 5'-CAC CCA AGA ACA GGG TTT GT-3' (SEQ ID NO:21); mitochondrial transfer RNA-Leu (URR) rev, 5'-TGG CCA TGG GTA TGT TGT TA-3' (SEQ ID NO:22); B2M fwd, 5'-TGC TGT CTC CAT GTT TGA TGT ATCT-3' (SEQ ID NO:23); and B2M rev, 5'-TCT CTG CTC CCC ACC TCT AAGT-3' (SEQ ID NO:24). All gene expression analyses were normalized against ACTB.

ChIP (Chromatin immunoprecipitation) assays: Aliquots $2.5 \times 10^6$ formaldehyde-fixed cells were resuspended in 50 µl nuclei isolation buffer (Abcam). Chromatin was digested by adding 15 U MNase (ThermoFisher) and incubating at 37° C. for 5 minutes. EDTA was added to stop the reaction. Digested chromatin was diluted in immunoprecipitation buffer (20 mM Tris-HCl pH 8.0, 2 mM EDTA, 150 mM NaCl, 0.1% Triton X-100, and 5 mM sodium butyrate) with EDTA-free protease inhibitors (Millipore) and pre-cleared with Protein G Agarose (Millipore) for 1 hour at 4° C. Precleared chromatin was immunoprecipitated overnight at 4° C. with antibodies against either ARID5B (NBP1-83622, Novus Biologicals), RNA polymerase II CTD repeat YSPT-SPS (SEQ ID NO:26) (phospho S5; ab5131; Abcam) or histone H3 (dimethyl K9; ab1220; Abcam). Samples were washed and eluted, and cross-links were reversed with a 4 hour incubation at 65° C. DNA was precipitated and analyzed by qRT-PCR.

NK cell effector function assays: For determination of NK cell degranulation, ARID5B shRNA and control NK-92 cells were cultured alone or with K562 target cells at a 1:1 ratio for 4 hours. Cells were then fixed and analyzed by FACS for surface CD107a expression and intracellular expression of IFN-γ. For additional determination of IFN-γ production, cells were incubated overnight with 5 ng/ml IL-12 (Peprotech) and 50 ng/ml IL-18 (R&D Systems) before staining.

Statistical Analysis: Statistics were calculated with GraphPad Prism (v5.0). Data are expressed as the mean±S.E.M. Differences between groups were determined by Student's t test. P-values<0.05 were considered statistically significant (*p<0.05, **p<0.01).

REFERENCES

Baba, A., F. Ohtake, Y. Okuno, K. Yokota, M. Okada, Y. Imai, M. Ni, C. A. Meyer, K. Igarashi, J. Kanno, et al. 2011. PKA-dependent regulation of the histone_lysine demethylase complex PHF2-ARID5B. *Nat. Cell Biol.* 13:668-675.

Bantug, G. R., M. Fischer, J. Grahlert, M. L. Balmer, G. Unterstab, L. Develioglu, R. Steiner, L. Zhang, A. S. H. Costa, P. M. Gubser, et al. 2018. Mitochondria-Endoplasmic Reticulum Contact Sites Function as Immunometabolic Hubs that Orchestrate the Rapid Recall Response of Memory CD8+ T Cells. *Immunity.* 48:542-555.e6.

Buck, M. D., D. O'Sullivan, R. I. Klein Geltink, J. D. Curtis, C. H. Chang, D. E. Sanin, J. Qiu, O. Kretz, D. Braas, G. J. van der Windt, et al. 2016. Mitochondrial Dynamics Controls T Cell Fate through Metabolic Programming. *Cell.* 166:63-76.

Champagne, D. P., K. M. Hatle, K. A. Fortner, A. D'Alessandro, T. M. Thornton, R. Yang, D. Torralba, J. Tomas-Cortazar, Y. W. Jun, K. H. Ahn, et al. 2016. Fine-Tuning of CD8(+) T Cell Mitochondrial Metabolism by the Respiratory Chain Repressor MCJ Dictates Protection to Influenza Virus. *Immunity.* 44:1299-1311.

Cichocki, F., S. Cooley, Z. Davis, T. E. DeFor, H. Schlums, B. Zhang, C. G. Brunstein, B. R. Blazar, J. Wagner, D. J. Diamond, et al. 2016. CD56dimCD57+ NKG2C+ NK cell expansion is associated with reduced leukemia relapse after reduced intensity HCT. *Leukemia.* 30:456-463.

Claussnitzer, M., S. N. Dankel, K. H. Kim, G. Quon, W. Meuleman, C. Haugen, V. Glunk, I. S. Sousa, J. L. Beaudry, V. Puviindran, et al. 2015. FTO Obesity Variant Circuitry and Adipocyte Browning in Humans. *N. Engl. J. Med.* 373:895-907.

Corat, M. A., H. Schlums, C. Wu, J. Theorell, D. A. Espinoza, S. E. Sellers, D. M. Townsley, N. S. Young, Y. T. Bryceson, C. E. Dunbar, and T. Winkler. 2017. Acquired somatic mutations in PNH reveal long-term maintenance of adaptive NK cells independent of HSPCs. *Blood.* 129:1940-1946.

Cunningham, J. T., J. T. Rodgers, D. H. Arlow, F. Vazquez, V. K. Mootha, and P. Puigserver. 2007. mTOR controls mitochondrial oxidative function through a YY1-PGC-1alpha transcriptional complex. *Nature.* 450:736-740.

Falkenberg, M., M. Gaspari, A. Rantanen, A. Trifunovic, N. G. Larsson, and C. M. Gustafsson. 2002. Mitochondrial transcription factors B1 and B2 activate transcription of human mtDNA. *Nat. Genet.* 31:289-294.

Foley, B., S. Cooley, M. R. Verneris, M. Pitt, J. Curtsinger, X. Luo, S. Lopez-Verges, L. L. Lanier, D. Weisdorf, and J. S. Miller. 2012. Cytomegalovirus reactivation after allogeneic transplantation promotes a lasting increase in educated NKG2C+ natural killer cells with potent function. Blood. 119:2665-2674.

Gerencser, A. A., A. Neilson, S. W. Choi, U. Edman, N. Yadava, R. J. Oh, D. A. Ferrick, D. G. Nicholls, and M. D. Brand. 2009. Quantitative microplate-based respirometry with correction for oxygen diffusion. *Anal. Chem.* 81:6868-6878.

Giménez-Cassina, A., and N. N. Danial. 2015. Regulation of mitochondrial nutrient and energy metabolism by BCL-2 family proteins. *Trends Endocrinol. Metab.* 26:165-175.

Gumá, M., A. Angulo, C. Vilches, N. Gomez-Lozano, N. Malats, and M. López-Botet. 2004. Imprint of human cytomegalovirus infection on the NK cell receptor repertoire. *Blood.* 104:3664-3671.

Haut, S., M. Brivet, G. Touati, P. Rustin, S. Lebon, A. Garcia-Cazorla, J. M. Saudubray, A. Boutron, A. Legrand, and A. Slama. 2003. A deletion in the human QP-C gene causes a complex III deficiency resulting in hypoglycaemia and lactic acidosis. *Hum. Genet.* 113:118-122.

Huss, J. M., I. P. Torra, B. Staels, V. Giguère, and D. P. Kelly. 2004. Estrogen-related receptor alpha directs peroxisome proliferator-activated receptor alpha signaling in the transcriptional control of energy metabolism in cardiac and skeletal muscle. *Mol. Cell. Biol.* 24:9079-9091.

Kägi, D., B. Ledermann, K. Bürki, P. Seiler, B. Odermatt, K. J. Olsen, E. R. Podack, R. M. Zinkernagel, and H. Hengartner. 1994. Cytotoxicity mediated by T cells and natural killer cells is greatly impaired in perforin-deficient mice. *Nature.* 369:31-37.

Kortschak, R. D., P. W. Tucker, and R. Saint. 2000. ARID proteins come in from the desert. *Trends Biochem. Sci.* 25:294-299.

Lahoud, M. H., S. Ristevski, D. J. Venter, L. S. Jermiin, I. Bertoncello, S. Zavarsek, S. Hasthorpe, J. Drago, D. de Kretser, P. J. Hertzog, and I. Kola. 2001. Gene targeting of Desrt, a novel ARID class DNA-binding protein, causes growth retardation and abnormal development of reproductive organs. *Genome Res.* 11:1327-1334.

Larsson, N. G., J. Wang, H. Wilhelmsson, A. Oldfors, P. Rustin, M. Lewandoski, G. S. Barsh, and D. A. Clayton. 1998. Mitochondrial transcription factor A is necessary for mtDNA maintenance and embryogenesis in mice. *Nat. Genet.* 18:231-236.

Lee, J., T. Zhang, I. Hwang, A. Kim, L. Nitschke, M. Kim, J. M. Scott, Y. Kamimura, L. L. Lanier, and S. Kim. 2015. Epigenetic modification and antibody-dependent expansion of memory-like NK cells in human cytomegalovirus-infected individuals. *Immunity.* 42:431-442.

Leong, W. Z., S. H. Tan, P. C. T. Ngoc, S. Amanda, A. W. Y. Yam, W. S. Liau, Z. Gong, L. N. Lawton, D. G. Tenen, and T. Sanda. 2017. ARID5B as a critical downstream target of the TAL1 complex that activates the oncogenic transcriptional program and promotes T-cell leukemogenesis. *Genes Dev.* 31:2343-2360.

Li, F., Y. Wang, K. I. Zeller, J. J. Potter, D. R. Wonsey, K. A. O'Donnell, J. W. Kim, J. T. Yustein, L. A. Lee, and C. V. Dang. 2005. Myc stimulates nuclearly encoded mitochondrial genes and mitochondrial biogenesis. *Mol. Cell. Biol.* 25:6225-6234.

Liu, Y., L. M. Reynolds, J. Ding, L. Hou, K. Lohman, T. Young, W. Cui, Z. Huang, C. Grenier, M. Wan, et al. 2017. Blood monocyte transcriptome and epigenome analyses reveal loci associated with human atherosclerosis. *Nat. Commun.* 8:393.

Lopez-Vergès, S., J. M. Milush, B. S. Schwartz, M. J. Pando, J. Jarjoura, V. A. York, J. P. Houchins, S. Miller, S. M. Kang, P. J. Norris, et al. 2011. Expansion of a unique CD57+NKG2Chi natural killer cell subset during acute human cytomegalovirus infection. *Proc. Natl. Acad. Sci. USA.* 108:14725-14732.

Marçais, A., J. Cherfils-Vicini, C. Viant, S. Degouve, S. Viel, A. Fenis, J. Rabilloud, K. Mayol, A. Tavares, J. Bienvenu, et al. 2014. The metabolic checkpoint kinase mTOR is essential for IL-15 signaling during the development and activation of NK cells. *Nat. Immunol.* 15:749-757.

Mookerjee, S. A., A. S. Divakaruni, M. Jastroch, and M. D. Brand. 2010. Mitochondrial uncoupling and lifespan. *Mech. Ageing Dev.* 131:463-472.

Nabekura, T., and L. L. Lanier. 2016. Tracking the fate of antigen-specific versus cytokine-activated natural killer cells after cytomegalovirus infection. *J. Exp. Med.* 213:2745-2758.

Nicholls, D. G. 2009. Spare respiratory capacity, oxidative stress and excitotoxicity. *Biochem. Soc. Trans.* 37:1385-1388.

Perry, S. W., J. P. Norman, J. Barbieri, E. B. Brown, and H. A. Gelbard. 2011. Mitochondrial membrane potential probes and the proton gradient: a practical usage guide. *Biotechniques.* 50:98-115.

Puigserver, P., Z. Wu, C. W. Park, R. Graves, M. Wright, and B. M. Spiegelman. 1998. A cold-inducible coactivator of nuclear receptors linked to adaptive thermogenesis. *Cell.* 92:829-839.

Redondo-Pachón, D., M. Crespo, J. Yélamos, A. Muntasell, M. J. Pérez-Sáez, S. Pérez-Fernández, J. Vila, C. Vilches, J. Pascual, and M. López-Botet. 2017. Adaptive NKG2C+ NK Cell Response and the Risk of Cytomegalovirus Infection in Kidney Transplant Recipients. *J. Immunol.* 198:94-101.

Saeed, S., J. Quintin, H. H. Kerstens, N. A. Rao, A. Aghajanirefah, F. Matarese, S. C. Cheng, J. Ratter, K. Berentsen, M. A. van der Ent, et al. 2014. Epigenetic programming of monocyte-to-macrophage differentiation and trained innate immunity. *Science.* 345:1251086.

Schlums, H., F. Cichocki, B. Tesi, J. Theorell, V. Beziat, T. D. Holmes, H. Han, S. C. Chiang, B. Foley, K. Mattsson, et al. 2015. Cytomegalovirus infection drives adaptive epigenetic diversification of NK cells with altered signaling and effector function. *Immunity.* 42:443-456.

Schlums, H., M. Jung, H. Han, J. Theorell, V. Bigley, S. C. Chiang, D. S. Allan, J. K. Davidson-Moncada, R. E. Dickinson, T. D. Holmes, et al. 2017. Adaptive NK cells can persist in patients with GATA2 mutation depleted of stem and progenitor cells. *Blood.* 129:1927-1939. Sentman, C. L., J. R. Shutter, D. Hockenbery, O. Kanagawa, and S. J. Korsmeyer. 1991. bcl-2 inhibits multiple forms of apoptosis but not negative selection in thymocytes. *Cell.* 67:879-888.

Sun, J. C., J. N. Beilke, and L. L. Lanier. 2009. Adaptive immune features of natural killer cells. *Nature.* 457:557-561.

van der Windt, G. J., B. Everts, C. H. Chang, J. D. Curtis, T. C. Freitas, E. Amiel, E. J. Pearce, and E. L. Pearce.

2012. Mitochondrial respiratory capacity is a critical regulator of CD8+ T cell memory development. Immunity. 36:68-78.

van der Windt, G. J., D. O'Sullivan, B. Everts, S. C. Huang, M. D. Buck, J. D. Curtis, C. H. Chang, A. M. Smith, T. Ai, B. Faubert, et al. 2013. CD8 memory T cells have a bioenergetic advantage that underlies their rapid recall ability. Proc. Natl. Acad. Sci. USA. 110:14336-14341.

Vivier, E., D. H. Raulet, A. Moretta, M. A. Caligiuri, L. Zitvogel, L. L. Lanier, W. M. Yokoyama, and S. Ugolini. 2011. Innate or adaptive immunity? The example of natural killer cells. Science. 331:44-49.

Whitson, R. H., T. Huang, and K. Itakura. 1999. The novel Mrf-2 DNA-binding domain recognizes a five-base core sequence through major and minor-groove contacts. Biochem. Biophys. Res. Commun. 258:326-331.

Whitson, R. H., W. Tsark, T. H. Huang, and K. Itakura. 2003. Neonatal mortality and leanness in mice lacking the ARID transcription factor Mrf-2. Biochem. Biophys. Res. Commun. 312:997-1004.

Zhang, T., J. M. Scott, I. Hwang, and S. Kim. 2013. Cutting edge: antibody-dependent memory-like NK cells distinguished by FcRγ deficiency. J. Immunol. 190:1402-1406.

---

We claim:

1. An isolated population of Natural Killer (NK) cells comprising a recombinant nucleic acid encoding an AT-rich interaction domain 5B (ARID5B) polypeptide operably linked to a heterologous promoter, wherein the NK cells exhibit increased expression of said ARID5B polypeptide relative to a wild-type NK cell.

2. The population of claim 1, wherein the NK cells are primary NK cells or NK-92 cells.

3. The population of claim 1, wherein the NK cells are CD3$^-$, TCR$^-$, CD56$^+$, and NKp46$^+$.

4. The population of claim 1, wherein the NK cells are differentiated in vitro from stem cells, hematopoietic stem or progenitor cells, or progenitor cells.

5. The population of claim 1, wherein the NK cells are differentiated in vitro from a CD34$^+$ hemogenic endothelium cell, a multipotent progenitor cell, or a NK progenitor cell.

6. The population of claim 1, wherein the NK cells are differentiated in vitro from induced pluripotent stem cells.

7. The population of claim 1, wherein the NK cells comprise a recombinant nucleic acid encoding a T-cell receptor (TCR) or a chimeric antigen receptor (CAR).

8. The population of claim 1, wherein the NK cells are produced in vitro or ex vivo from immune cells isolated from or comprised in peripheral blood.

9. The population of claim 1, wherein the NK cells are human.

10. A cell composition comprising the population of NK cells of claim 1 and a carrier or excipient.

11. A pharmaceutical composition comprising the population of NK cells of claim 1 and a pharmaceutically acceptable carrier or excipient.

12. A therapeutic composition for treating a tumor in a subject comprising the population of NK cells of claim 1, wherein the NK cells are suspended in a pharmaceutically acceptable medium suitable for injection.

* * * * *